(12) United States Patent
Wei

(10) Patent No.: US 8,232,228 B2
(45) Date of Patent: Jul. 31, 2012

(54) METHOD FOR INCREASING THE EFFICACY OF AGRICULTURAL CHEMICALS

(75) Inventor: Zhong-Min Wei, Kirkland, WA (US)

(73) Assignee: Plant Health Care, Inc., Pittsburgh, PA (US)

( * ) Notice: Subject to any disclaimer, the term of this patent is extended or adjusted under 35 U.S.C. 154(b) by 1282 days.

(21) Appl. No.: 10/538,274

(22) PCT Filed: Dec. 15, 2003

(86) PCT No.: PCT/US03/40089
§ 371 (c)(1),
(2), (4) Date: Sep. 28, 2006

(87) PCT Pub. No.: WO2004/057957
PCT Pub. Date: Jul. 15, 2004

(65) Prior Publication Data
US 2007/0037705 A1    Feb. 15, 2007

Related U.S. Application Data

(60) Provisional application No. 60/433,893, filed on Dec. 16, 2002.

(51) Int. Cl.
*A01N 25/26* (2006.01)
*A01N 25/00* (2006.01)
*A01N 63/00* (2006.01)

(52) U.S. Cl. ............... 504/100; 504/116.1; 504/118

(58) Field of Classification Search .................. None
See application file for complete search history.

(56) References Cited

U.S. PATENT DOCUMENTS

| | | | | |
|---|---|---|---|---|
| 5,776,889 A | * | 7/1998 | Wei et al. | 514/2 |
| 5,859,324 A | * | 1/1999 | Wei et al. | 800/298 |
| 6,001,959 A | * | 12/1999 | Bauer et al. | 530/300 |
| 6,172,184 B1 | | 1/2001 | Collmer et al. | |
| 6,277,814 B1 | * | 8/2001 | Qiu et al. | 514/2 |
| 6,960,705 B2 | * | 11/2005 | Wei et al. | 800/301 |
| 2001/0004628 A1 | * | 6/2001 | Ruegg | 504/129 |
| 2002/0059658 A1 | * | 5/2002 | Wei et al. | 800/278 |
| 2002/0062500 A1 | * | 5/2002 | Fan et al. | 800/288 |

FOREIGN PATENT DOCUMENTS

| | | | |
|---|---|---|---|
| WO | WO 96/23411 | | 8/1996 |
| WO | WO 98/37752 | | 9/1998 |
| WO | WO-9837752 | * | 9/1998 |
| WO | WO 99/35913 | | 7/1999 |
| WO | WO 01/67865 | | 9/2001 |

OTHER PUBLICATIONS

Bailey et al., "Factors Influencing the Herbicidal Activity of Nep1, a Fungal Protein That Induces the Hypersensitive Response in *Centaurea maculosa*," Weed Science 48(6):776-785 (2000).
Tosun et al., "The Effect of Harpin EA as Plant Activator in Control of Bacterial and Fungal Diseases of Tomato," Acta Hort. 613:251-254 (2003).
Supplementary European Search Report dated Jan. 5, 2010.

* cited by examiner

*Primary Examiner* — Alton Pryor
(74) *Attorney, Agent, or Firm* — LeClairRyan, a Professional Corporation

(57) ABSTRACT

The present invention is directed to increasing the efficacy of agricultural chemicals. This can be achieved by applying at least one agricultural chemical to a plant or plant seed under conditions effective for the agricultural chemical to perform its intended function and applying at least one hypersensitive response elicitor protein or polypeptide to the plant or plant seed under conditions effective to increase the efficacy of the agricultural chemical. Alternatively, the present invention relates to a method for increasing the efficacy of agricultural chemicals by applying an agricultural chemical to a transgenic plants or transgenic seeds transformed with nucleic acid molecule which encodes a hypersensitive response elicitor protein or polypeptide, wherein the agricultural chemical is applied under conditions effective for the agricultural chemical to perform its intended function but with increased efficacy.

24 Claims, No Drawings

METHOD FOR INCREASING THE EFFICACY OF AGRICULTURAL CHEMICALS

This application is a national stage application under 35 U.S.C. §371 from PCT Application No. PCT/US03/40089, filed Dec. 15, 2003, which claims the priority benefit of U.S. Provisional Patent Application No. 60/433,893, filed Dec. 16, 2002.

FIELD OF INVENTION

The present invention relates to methods of increasing the efficacy of commonly used agricultural chemicals.

BACKGROUND

Modern agricultural practices rely heavily on the use of chemical inputs to maintain and increase productivity. Agricultural chemical inputs can be broadly categorized as pesticides, fertilizers, and plant growth regulators. Based on monetary expenditure, as well as physical volumes, the vast majority of chemical inputs are in the form of pesticides and fertilizers. In the common agricultural sense, pests are any organisms that contribute to a loss of value or productivity in a crop. Pesticides can be categorized into; insecticides, fungicides, herbicides, as well as minor categories such as acaricides, avicides, virucides, and nematicides. In 1996, U.S. farmers spent over $8.5 billion on pesticides. This translates to the use of over 355 million pounds of herbicides, 70 million pounds of insecticides, and 180 million pounds of fungicides and other pesticides in 1996 alone (Fernandez-Conejo and Jans, "Pest Management in the U.S. Agriculture." Resource Economics Division, Economic Research Service, U.S. Department of agriculture. Agricultural Handbook No. 717.). With some exceptions, fertilizers are typically characterized as substances containing plant macronutrients or plant micronutrients, and are used in as proportionally as large of volumes as pesticides. In 1997, approximately 22 million tons of nutrients were applied in the United States alone (Data from the Economic Research Service, U.S. Department of Agriculture). Plant growth regulators are a class of agricultural chemical inputs whose use is minor compared to pesticides and fertilizers. Nonetheless, plant growth regulators have significant importance in specific agricultural sectors such as fruit production and ornamentals.

Though the increase in use of agricultural chemicals has directly contributed to an increase in productivity, the increased productivity has not come without a price. Most pesticides present inherent human and environmental health risks. Increasingly, municipalities are identifying hazardous agricultural chemicals, or their residues, in local water sources, streams, and lakes. In addition, the high volumes of pesticides being applied results in the development of pest resistance to the agricultural chemical being applied. Incidences of pest resistance have been documented in most classes of pesticide and a wide range of crop types. Resistance occurs after persistent use of a pesticide or closely related pesticides has decimated a local population of pests, but left a small sub-population of the same pest surviving. The sub-population, either through human pressure or natural divergence of ecotypes, has evolved to be less affected or resistant to the pesticide or closely related pesticides. After repeated cycles of heavy use of the pesticide, decimation of the local population, and survival of the resistant sub-populations, the resistant sub-population eventually multiplies to become the dominant population. The end result being, an entire pest population that is resistant to a given pesticide or closely related pesticides. A once effective and important pesticide is essentially rendered useless to the farmer or commercial grower. Prior to recognition of the actual existence of a resistant pest, the grower having recognized a decrease in efficacy of a pesticide will often intuitively increase the amount of pesticide being applied. Thus, compounding the situation by furthering the propagation of resistant pest through increased use of the pesticide, decreasing the profitability of the crop because of increased purchases of chemical inputs, and simultaneously increasing the human and environmental health risks.

Greater crop yields, resulting from an increased use of fertilizers, have not come without detrimental effects either. Fertilizers are applied to cropland to replenish or add nutrients that are needed by an existing or future crop. The vast majority of the nutrients applied are in the form of nitrogen, phosphorus, and potash (i.e. potassium). Depending on a combination of factor such as the soil's chemical structure, pH, and texture; fertilizer components can be highly susceptible to leaching. Leaching occurs when the amount of water present in the soil, either from irrigation of rainfall, is greater than the soil's water-holding capacity. When this occurs, solubilized fertilizer components are carried low into the soil and out of the plant root zone, thus effectively removing the nutrients for use by the plant. Nitrate-nitrogen ($NO_3^-$) is particularly prone to leaching, and can result in hazardous nitrate accumulation in groundwater. In the U.S. and abroad, cropland is commonly over-fertilized. Soil nutrient analysis is often viewed as timely and not economically feasible. Thus, fertilizers are often applied at regular intervals regardless of their need. As with pesticides, the over use of the fertilizers has potentially far reaching detrimental effect on agricultural profitability and risk to environmental health.

In recent years, farmers and agricultural researchers have begun to develop programs and techniques to aid in combating the cycles of increased chemical inputs and decreased profitability. These programs and techniques are commonly referred to as Integrated Pest Management (IPM), or more broadly, Integrated Crop Management (ICM). ICM programs and techniques are being advanced by a range of organizations including; the USDA, land-grant universities and the private sector. ICM Programs are specifically designed with respect to crop type, local environmental conditions, and local pest pressures. In contrast to previous agricultural practices, ICM practices draw on a broad range of techniques and tools including; early and persistent monitoring of pest populations, establishment of acceptable pest population thresholds, the development of chemical control programs that routinely rotate the chemicals being utilized, establishment of cultural control techniques (e.g. adjusting planting and harvesting dates, no-till systems, crop rotation, etc.), promotion of the use of specific plant varieties or transgenic plants, and the development of biological controls techniques (e.g. use of beneficial insects, use of pheromones traps, use of live microorganisms such as *Bacillius thuringensis*, etc.). Although ICM practices show great promise for combating many of the problems associated with the high chemical input of modern agricultural practices, the ability to increase the efficacy of the commonly used agricultural chemicals would greatly aid in the over all effort. Increased efficacy would provide greater pest control and/or facilitate decreases in the volume of agricultural chemicals used.

As evident from the above discussion, modern agricultural practices dictate the need to apply several agricultural chemicals, often repeatedly, to a single crop over the course of a growing season. To facilitate this need to apply numerous chemicals to a single crop, it has become routine practice to make what is referred to as tank mixes. Tank mixes are a single application of one or more chemical at the same time. The agricultural chemicals that are desired to be applied are combined into one tank, mixed, soluablized if needed, and applied to the crop. There are limitations to this practice in that some agricultural chemicals are not compatible and may precipitate, become inactive, or decrease the efficacy of other chemicals when mixed together. Pesticide interactions are typically characterized as additive, synergistic, antagonistic, and enhancement. Additive effects occur when the combination of two pesticides produces the same amount of control as the combined effects of each of the chemicals applies independently. Synergistic effects occur when the combined effects of the chemicals is greater than the additive effects. It is assumed that in synergistic pesticide interactions the chemicals are not neutral to one another, and to some extent are chemically interacting with one another. Antagonistic effects are those resulting when the combination of chemicals is less than if the chemicals were used individually. Enhanced effects can occur when a pesticide is combined with an additive that is not a pesticide and the resulting control of the desired pest is greater than if the pesticide was used individually. Factor such as the quantity of water used, the order of mixing the chemicals, and the addition of ajuvants may also affect the utility of a tank mix (Petroff, "Pesticide Interaction and Compatibility," Montana State University).

The present invention is directed towards improving the efficacy of agricultural chemicals.

SUMMARY OF THE INVENTION

The present invention relates to a method for increasing the efficacy of agricultural chemicals. In one embodiment of the present invention, the method is carried out by applying at least one agricultural chemical and at least one least one hypersensitive response elicitor protein or peptide to a plant or plant seed under conditions effective to increase the efficacy of the agricultural chemical.

In addition, the present invention relates to a method for increasing the efficacy of agricultural chemicals by applying one or more agricultural chemicals to a transgenic plants or transgenic seeds transformed with a nucleic acid molecule which encodes a hypersensitive response elicitor protein or polypeptide under conditions effective for the agricultural chemical to perform its intended function but with increased efficacy.

By the present invention, the efficacy of an agricultural chemical is increased. In achieving this objective, the present invention enables the grower to more effectively manage their crops with respect to fertilizers and plant growth regulators and to more effectively control pests such as insects, fungus, disease, and weeds. As a result of the increased efficacy in controlling common pest problems, growers can reduce yield losses resulting from pest problems. In addition, the present invention enables growers to utilize lower quantities of commonly utilized agricultural chemicals while maintaining or increasing yields. The reduction of agricultural chemical use will also result in profound health and ecological benefits.

DETAILED DESCRIPTION OF THE INVENTION

The present invention relates to a method for increasing the efficacy of agricultural chemicals. In one embodiment of the present invention, the method is carried out by applying at least one agricultural chemical and at least one least one hypersensitive response elicitor protein or peptide to a plant or plant seed under conditions effective to increase the efficacy of the agricultural chemical.

Agricultural chemicals, according to the present invention, can be divided into several broad categories pesticides, fertilizers, and plant growth regulators. Pesticides, perhaps the most diverse category of agricultural chemicals, can be subdivided into categories based on the type of pest or organism which they are intended to control, such as; insecticides, intended for the control of insect; fungicides, intended for the control of fungi; herbicides, intended for the control of noxious weeds and plants; acaricides, intended for the control of arachnids or spiders; virucides intended for the control of viruses; and nematicides, intended for the control of nematodes.

For use in accordance with this method, suitable insecticides include but, are not limited to those listed in Table 1.

TABLE 1

Common Agricultural Insecticides

| Class of Active Ingredient | Common Name of Active Ingredient | Active ingredient | Example Product Name |
|---|---|---|---|
| carbamate | Aldricarb (ISO) | 2-methyl-2-(methylthio)propanal O-[(methylamino)carbonyl]oxime (CAS) | Temik ® (Aventis CropScience, Research Triangle Park, NC) |
| organochlorine | Endosulfan (ISO) | 6,7,8,9,10,10-hexachloro-1,5,5a,6,9,9a-hexahydro-6,9-methano-2,4,3-benzodioxathiepin 3-oxide (CAS) | Thiodan ® (Aventis CropScience, Research Triangle Park, NC) |
| nicotinoid | Imidacloprid (ISO) | 1-[(6-chloro-3-pyridinyl)methyl]-N-nitro-2-imidazolidinimine (CAS) | Merit ® (Bayer Ag, Leverkusen, Germany) |
| phosphoramidothioate | Acephate (ISO) | O,S-dimethyl acetylphosphoramidothioate (CAS) | Orthene ® (Valent U.S.A. Corp., Walnut Creek, CA) |
| organothiophosphate | Dimethoate (ISO) | O,O-dimethyl S-[2-(methylamino)-2-oxoethyl] phosphorodithioate (CAS) | Roxion ® (BASF Corp., Research Triangle Park, NC) |
| pyrethroid | Permethrin (ISO) | (3-phenoxyphenyl)methyl 3-(2,2-dichloroethenyl)-2,2-dimethylcyclopropanecarboxylate (CAS) | Ambush ® (Syngenta, Greensboro NC) |

Table 1 is intended as an example. Alternative example product names and classifications exist for the active ingredients cited and would fall within the scope of the present invention.

For use in accordance with this method, suitable fungicides include those listed in Table 2. In addition to Table 2, suitable fungicides include various forms of organic and inorganic copper. Examples of suitable copper compounds include, copper ammonium, copper hydroxide, copper oxychloride, and copper-zinc-chromate.

Table 2 is intended as an example. Alternative example product names and classifications exist for the active ingredients cited and would fall within the scope of the present invention.

For use in accordance with this method, suitable herbicides include, but are not limited to those listed in Tables 3 and 4. Table 3 outlines a Site of Action Classification of Herbicides and is based on the classification system developed by the Weed Science Society of America (WSSA). The herbicide's site of action is defined as the specific biochemical process in the plant that the herbicide acts upon or disrupts. For example, an herbicide containing the active ingredient primisulfuron,

TABLE 2

Common Agricultural Fungicides

| Class of Active Ingredient | Common Name of Active Ingredient | Active ingredient | Example Product Name |
|---|---|---|---|
| aromatic | Chlorothalonil (ISO) | Tetrachloroisophthalonitrile (IUPAC) | Bravo ® (Syngenta, Greensboro NC) |
| copper | copper hydroxide | copper hydroxide ($Cu(OH)_2$) (CAS) | Kocide ® (Griffin L.L.C., Valdosta GA) |
| sulfur | Flowers of Sulfur | sulfur | Kumulus ® (BASF Corp., Research Triangle Park, NC) |
| aliphatic nitrogen | Cymoxanil (ISO) | 2-cyano-N-[(ethylamino)carbonyl]-2-(methoxyimino)acetamide (CAS) | Curzate ® (DuPont Crop Protection, Wilmington, DE) |
| benzimidazole | Thiabendazole (ISO) | 2-(4-thiazolyl)-1H-benzimidazole (CAS) | Thiabendazole ® (Syngenta, Greensboro NC) |
| dicarboximide | Captan (ISO) | 3a,4,7,7a-tetrahydro-2-[(trichloromethyl)thio]-1H-isoindole-1,3(2H)-dione (CAS) | Captan ® (Syngenta, Greensboro NC) |
| dicarboximide | Vinclozolin (ISO) | 3-(3,5-dichlorophenyl)-5-ethenyl-5-methyl-2,4-oxazolidinedione (CAS) | Ronilan ® (BASF Corp., Research Triangle Park, NC) |
| dithiocarbamate | Mancozeb (ISO) | [[1,2-ethanediylbis[carbamodithioato]](2-)]manganese mixture with [[1,2-ethanediylbis[carbamodithioato]](2-)] zinc (CAS) | Dithane ® (Rohm and Haas Co., Philadelphia, PA) |
| dithiocarbamate | Maneb (ISO) | [[1,2-ethanediylbis[carbamodithioato]](2-)] manganese (CAS) | Manex ® (Griffin L.L.C., Valdosta GA) |
| dithiocarbamate | Metiram (JMAFF) | zinc ammoniate ethylenebis(ditbiocarbamate) - poly(ethylenethiuram disulfide) (IUPAC) | Polyram ® (BASF Corp., Research Triangle Park, NC) |
| dithiocarbamate | Thiram (ISO) | tetramethylthioperoxydicarbonic diamide ($[[(CH_3)_2N]C(S)]_2S_2$) (CAS) | Thiram ® (BASF Corp., Research Triangle Park, NC) |
| dithiocarbamate | Ziram (ISO) | (T-4)-bis(dimethylcarbamoditbioato-S,S')zinc | Ziram ® (UBC Agrochemicals, Ghent, Belgium) |
| imidazole, dicarboximide | Iprodione (ISO) | 3-(3,5-dichlorophenyl)-N-(1-methylethyl)-2,4-dioxo-1-imidazolidinecarboxamide (CAS) | Rovral ® (Aventis CropScience, Research Triangle Park, NC) |
| organophosphate | Fosetyl-aluminum (ISO) | ethyl hydrogen phosphonate(CAS) as an aluminum salt | Alientte ® (Aventis CropScience, Research Triangle Park, NC) |
| strobin | Azoxystrobin (ISO) | ($\alpha$E)-methyl 2-[[6-(2-cyanophenoxy)-4-pyrimidinyl]oxy]-$\alpha$-(methoxymethylene)benzeneacetate (CAS) | Abound ® (Syngenta, Greensboro NC) |
| anilide | Metalaxyl (ISO) | methyl N-(2,6-dimethylphenyl)-N-(methoxyacetyl)-DL-alaninate (CAS) | Ridomil ® (Syngenta, Greensboro NC) | has a site of action classification number 2. Table 3 indicates that a Classification Number 2 has as its site of action acetolactate synthase inhibition.

TABLE 3

Herbicide Site of Action and Classification Numbers.

| Site of Action Classification No. | Description of Site of Action |
|---|---|
| 1 | ACCase = acetyl-CoA carboxylase inhibitor |
| 2 | ALS = actolactate synthase inhibitor |
| 3 | MT = microtubule assembly inhibitor |
| 4 | GR = growth regulator |
| 5 | PSII(A) = photosynthesis II, binding site A inhibitor |
| 6 | PSII(B) = photosynthesis II, binding site B inhibitor |
| 7 | PSII(C) = photosynthesis II, binding site C inhibitor |
| 8 | SHT = shoot inhibitor |
| 9 | EPSP = enolpyruvyl-shikimate-phosphate synthase inhibitor |
| 10 | GS = glutamine synthase inhibitor |
| 12 | PDS = phytoene desaturase synthase inhibitor |
| 13 | DITERP = diterpene inhibitor |
| 14 | PPO = protoporphyrinogen oxidase inhibitor |
| 15 | SHT/RT = shoot and root inhibitor |
| 22 | ED = photosystem 1 electron diverter |
| 28 | HPPD = hydroxyphenlypyruvate dioxygenase synthesis inhibitor |

TABLE 4

Common Agricultural Herbicides

| Site of Action | Class of Active Ingredient | Common Name of Active Ingredient | Active ingredient | Example Product Name |
|---|---|---|---|---|
| 1 | Cyclohexene Oxime | Sethoxydim (ISO) | 2-[1-(ethoxyimino)butyl]-5-[2-(ethylthio)propyl]-3-hydroxy-2-cyclohexen-1-one (CAS) | Poast ® (BASF Corp., Research Triangle Park, NC) |
| 1 | Phenoxy | Quizalofop-P (ISO) | (R)-2-[4-[(6-chloro-2-quinoxalinyl)oxy]phenoxy]propanoic acid (CAS) | Assure II ® (DuPont Crop Protection, Wilmington, DE) |
| 2 | Sulfonylurea | Primisulfuron (ISO) | 2-[[[[[4,6-bis(difluoromethoxy)-2-pyrimidinyl]amino]carbonyl]amino]sulfonyl]benzoic acid (CAS) | Beacon ® (Syngenta, Greensboro NC) |
| 2 | Imidazolinone | Imazamox (ISO) | 2-[4,5-dihydro-4-methyl-4-(1-methylethyl)-5-oxo-1H-imidazol-2-yl]-5-(methoxymethyl)-3-pyridinecarboxylic acid (CAS) | Raptor ® (BASF Corp., Research Triangle Park, NC) |
| 3 | Dinitroaniline | Trifluralin (ISO) | 2,6-dinitro-N,N-dipropyl-4-(trifluoromethyl)benzenamine (CAS) | Passport ® (BASF Corp., Research Triangle Park, NC) |
| 3 | Dinitroaniline | Pendimethalin (ISO) | N-(1-ethylpropyl)-3,4-dimethyl-2,6-dinitrobenzenamine (CAS) | Prowl ® (BASF Corp., Research Triangle Park, NC) |
| 4 | Phenoxy | 2,4-D (ISO) | (2,4-dichlorophenoxy)acetic acid (CAS) | Amsol ® (Aventis CropScience, Research Triangle Park, NC) |
| 4 | Benzoic acid | Dicamba (ISO) | 3,6-dichloro-2-methoxybenzoic acid (CAS) | Banvel ® (BASF Corp., Research Triangle Park, NC) |
| 5 | Triazine | Atrazine (ISO) | 6-chloro-N-ethyl-N'-(1-methylethyl)-1,3,5-triazine-2,4-diamine (CAS) | Atrazine ® (Syngenta, Greensboro NC) |
| 5 | Triazine | Cyanazine (ISO) | 2-[[4-chloro-6-(ethylamino)-1,3,5-triazin-2-yl]amino]-2-methylpropanenitrile (CAS) | Blandex ® (BASF Corp., Research Triangle Park, NC) |
| 6 | Nitrite | Bromoxylin (ISO) | 3,5-dibromo-4-hydroxybenzonitrile (CAS) | Buctril ® (Aventis CropScience, Research Triangle Park, NC) |
| 7 | Phenylurea | Diuron (ISO) | N'-(3,4-dichlorophenyl)-N,N-dimethylurea (CAS) | Karmex ® (Griffin L.L.C., Valdosta GA) |
| 8 | Thiocarbamate | EPTC (ISO) | S-ethyl dipropylcarbamothioate (CAS) | Eptam ® (Syngenta, Greensboro NC) |

TABLE 4-continued

Common Agricultural Herbicides

| Site of Action | Class of Active Ingredient | Common Name of Active Ingredient | Active ingredient | Example Product Name |
|---|---|---|---|---|
| 9 | Organophosphorus | Glyphosate (ISO) | N-(phosphonomethyl)glycine (CAS) | Roundup ® (Monsanto Co., St Louis MO) |
| 10 | Organophosphorus | Glufosinate (ISO) | 2-amino-4-(hydroxymethylphosphinyl)butanoic acid (CAS) | Liberty ® (Aventis CropScience, Research Triangle Park, NC) |
| 12 | Pyridazinone | Norflurazon (ISO) | 4-chloro-5-(methylamino)-2-[3-(trifluoromethyl)phenyl]-3(2H)-pyridazinone (CAS) | Zorial ® (Syngenta, Greensboro NC) |
| 13 | unclassified | Clomazone (ISO) | 2-[(2-chlorophenyl)methyl]-4,4-dimethyl-3-isoxazolidinone (CAS) | Command ® (FMC Corp., Philadelphia, PA) |
| 14 | Diphenyl ether | Fomesafen (ISO) | 5-[2-chloro-4-(trifluoromethyl)phenoxy]-N-(methylsulfonyl)-2-nitrobenzamide (CAS) | Reflex ® (Syngenta, Greensboro NC) |
| 15 | Chloroacetanilide | Alachlor (ISO) | 2-chloro-N-(2,6-diethylphenyl)-N-(methoxymethyl)acetamide (CAS) | Lasso ® (Monsanto Co., St. Louis MO) |
| 15 | Chloroacetanilide | Acetochlor (ISO) | 2-chloro-N-(ethoxymethyl)-N-(2-ethyl-6-methylphenyl)acetamide (CAS) | Surpass ® (Dow AgroScience LLC, Indianapolis, IN) |
| 22 | Quaternary ammonium | Diquat (ISO) | 6,7-dihydrodipyrido[1,2-α:2',1'-c]pyrazinediium (CAS) | Reglone ® (Syngenta, Greensboro NC) |
| 28 | Cyclopropylisoxazole | Isoxaflutole (ISO) | (5-cyclopropyl-4-isoxazolyl)[2-(methylsulfonyl)-4-(trifluoromethyl)phenyl]methanone (CAS) | Balance ® (Aventis CropScience, Research Triangle Park, NC) |

Table 4 is intended as an example. Alternative example product names and classifications exist for the active ingredients cited and would fall within the scope of the present invention.

For use in accordance with this method, suitable fertilizers include, but are not limited to those containing plant micronutrients (molybdenum, copper, zinc, manganese, iron, boron, cobalt, and chlorine) and plant macronutrients (sulfur, phosphorus, magnesium, calcium, potassium, and nitrogen). Numerous combinations and forms of plant macro and micronutrients exist and are available in a wide range of formulations. The predominant fertilizers used in agriculture contain various combinations and concentrations of nitrogen, phosphorus, and potassium. Micronutrient specific fertilizers are also common and may contain a single micronutrient or a combination of several micronutrients.

For use in accordance with this method, suitable plant growth regulators include, but are not limited to those containing various form and combinations of auxins, cytokinins, defoliants, gibberellins, ethylene releaser, growth inhibitors, growth retardants, and growth stimulators. Specific plant growth regulators include but are not limited to those listed in Table 5.

TABLE 5

Common Plant Growth Regulators

| Class of Active Ingredient | Common Name of Active Ingredient | Active ingredient | Example Product Name |
|---|---|---|---|
| Cytokinin | Zeatin | (E)-2-methyl-4-(1H-purin-6-ylamino)-2-buten-1-ol | |
| Defoliant | Thidiazuron (ISO) | N-phenyl-N'-1,2,3-thiadiazol-5-ylurea (CAS) | Dropp ® (Aventis CropScience, Research Triangle Park, NC) |
| Growth stimulator | Forchlorfenuron | N-(2-chloro-4-pyridinyl)-N'-phenylurea (CAS) | |
| Growth Inhibitor | Mepiquat (ISO) chloride | N,N-dimethylpiperdinum chloride (CAS) | Pix ® (BASF Corp., Research Triangle Park, NC) |
| Growth Inhibitor | Maleic Hydrazide (ISO-E) | 1,2-dihydro-3,6-pyridazinedione (CAS) | Sprout Stop ® (Drexel Chemical Co., Memphis, TN) |

TABLE 5-continued

Common Plant Growth Regulators

| Class of Active Ingredient | Common Name of Active Ingredient | Active ingredient | Example Product Name |
|---|---|---|---|
| Growth Retardant | Palclobutrazol (ISO) | (R*,R*)-β-[(4-chlorophenyl)methyl]-α-(1,1-dimethylethyl)-1H-1,2,4-triazole-1-ethanol (CAS) | Bonzi ® (Syngenta, Greensboro NC) |
| Difoliant, ethylene releaser | Ethephon (ANSI) | (2-chloroethyl)phosphonic acid (CAS) | Prep ® (Aventis CropScience, Research Triangle Park, NC) |
| Gibberellin | Gibberellic acid | (1α,2β,4aα,4bβ,10β)-2,4a,7-trihydroxy-1-methyl-8-methylenegibb-3-ene-1,10-dicarboxylic acid 1,4a-lactone (CAS) | RyzUp ® (Valent U.S.A. Corp., Walnut Creek, CA) |
| Auxin | α-naphthaleneacetic acid (ISO) | 1-naphthaleneacetic acid (CAS) | Tre-Hold ® (Amvac Chemical Co., New Port Beach, CA) |
| Auxin | IBA | Indole-3-butyric acid (CAS 8CI) | Seradix ® (Aventis CropScience, Research Triangle Park, NC) |
| Gibberellin | BAP + Gibberellic acid | N-(phenylmethyl)-1H-purine-6-amine and gibberellic acid | Accel ® (Agtrol International, Huston, TX) |
| | | (S)-trans-2-Amino-4-(2-aminoethoxy)-3-butenoic acid hydrochloride | ReTain ® (Valent U.S.A. Corp., Walnut Creek, CA) |

Table 5 is intended as an example. Alternative example product names and classifications exist for the active ingredients cited and would fall within the scope of the present invention.

For use in accordance with these methods, suitable hypersensitive response elicitor protein or polypeptide are from bacterial sources including, without limitation, *Erwinia* species (e.g., *Erwinia amylovora, Erwinia chrysanthemi, Erwinia stewartii, Erwinia carotovora,* etc.), *Pseudomonas* species (e.g., *Pseudomonas syringae, Pseudomonas solanacearum,* etc.), and *Xanthomonas* species (e.g., *Xanthomonas campestris*).

The hypersensitive response elicitor protein or polypeptide is derived, preferably, from *Erwinia chrysanthemi, Erwinia amylovora, Pseudomonas syringae, Pseudomonas solanacearum,* or *Xanthomonas campestris.*

A hypersensitive response elicitor protein or polypeptide from *Erwinia chrysanthemi* has an amino acid sequence corresponding to SEQ. ID. No. 1 as follows:

```
Met Gln Ile Thr Ile Lys Ala His Ile Gly Gly Asp Leu Gly Val Ser
1               5                   10                  15

Gly Leu Gly Ala Gln Gly Leu Lys Gly Leu Asn Ser Ala Ala Ser Ser
            20                  25                  30

Leu Gly Ser Ser Val Asp Lys Leu Ser Ser Thr Ile Asp Lys Leu Thr
        35                  40                  45

Ser Ala Leu Thr Ser Met Met Phe Gly Gly Ala Leu Ala Gln Gly Leu
        50              55                  60

Gly Ala Ser Ser Lys Gly Leu Gly Met Ser Asn Gln Leu Gly Gln Ser
65                  70                  75                  80

Phe Gly Asn Gly Ala Gln Gly Ala Ser Asn Leu Leu Ser Val Pro Lys
                85                  90                  95

Ser Gly Gly Asp Ala Leu Ser Lys Met Phe Asp Lys Ala Leu Asp Asp
            100                 105                 110

Leu Leu Gly His Asp Thr Val Thr Lys Leu Thr Asn Gln Ser Asn Gln
            115                 120                 125

Leu Ala Asn Ser Met Leu Asn Ala Ser Gln Met Thr Gln Gly Asn Met
            130                 135                 140

Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
```

-continued

```
Gly Asn Ala Ile Gly Met Gly Val Gly Gln Asn Ala Ala Leu Ser Ala
        180             185                 190
            195                 200                 205
Leu Ser Asn Val Ser Thr His Val Asp Gly Asn Asn Arg His Phe Val
    210             215                 220
Asp Lys Glu Asp Arg Gly Met Ala Lys Glu Ile Gly Gln Phe Met Asp
225                 230                 235                 240
Gln Tyr Pro Glu Ile Phe Gly Lys Pro Glu Tyr Gln Lys Asp Gly Trp
                245                 250                 255
Ser Ser Pro Lys Thr Asp Asp Lys Ser Trp Ala Lys Ala Leu Ser Lys
            260                 265                 270
Pro Asp Asp Asp Gly Met Thr Gly Ala Ser Met Asp Lys Phe Arg Gln
        275                 280                 285
Ala Met Gly Met Ile Lys Ser Ala Val Ala Gly Asp Thr Gly Asn Thr
    290                 295                 300
Asn Leu Asn Leu Arg Gly Ala Gly Gly Ala Ser Leu Gly Ile Asp Ala
305                 310                 315                 320
Ala Val Val Gly Asp Lys Ile Ala Asn Met Ser Leu Gly Lys Leu Ala
                325                 330                 335
Asn Ala
```

This hypersensitive response elicitor protein or polypeptide has a molecular weight of 34 kDa, is heat stable, has a glycine content of greater than 16%, and contains substantially no cysteine. This *Erwinia chrysanthemi* hypersensitive response elicitor protein or polypeptide is encoded by a DNA molecule having a nucleotide sequence corresponding to SEQ. ID. No. 2 as follows:

```
cgattttac

```
ccgccactttgtagataaagaagatcgcggcatggcgaaagagatcggccagtttatgga 1320
tcagtatccggaaatattcggtaaaccggaataccagaaagatggctggagttcgccgaa 1380
gacggacgacaaatcctgggctaaagcgctgagtaaaccggatgatgacggtatgaccgg 1440
cgccagcatggacaaattccgtcaggcgatgggtatgatcaaaagcgcggtggcgggtga 1500
taccggcaataccaacctgaacctgcgtggcgcgggcggtgcatcgctgggtatcgatgc 1560
ggctgtcgtcggcgataaaatagccaacatgtcgctgggtaagctggccaacgcctgata 1620
atctgtgctggcctgataaagcggaaacgaaaaagagacggggaagcctgtctcttttc 1680
ttattatgcggtttatgcggttacctggaccggttaatcatcgtcatcgatctggtacaa 1740
acgcacattttcccgttcatcgcgtcgttacgcgccacaatcgcgatggcatcttcctc 1800
gtcgctcagattgcgcggctgatggggaacgccgggtggaatatagagaaactcgccggc 1860
cagatggagacacgtctgcgataaatctgtgccgtaacgtgtttctatccgccccttag 1920
cagatagattgcggtttcgtaatcaacatgtaatgcggtccgcctgtgcgccggccgg 1980
gatcaccacaatattcatagaaagctgtcttgcacctaccgtatcgcgggagataccgac 2040
aaaatagggcagttttttgcgtggtatccgtggggtgttccggcctgacaatcttgagttg 2100
gttcgtcatcatctttctccatctgggcgacctgatcggtt                    2141
```

The above nucleotide and amino acid sequences are disclosed and further described in U.S. Pat. No. 5,850,015 to Bauer et al. and U.S. Pat. No. 5,776,889 to Wei et al., which are hereby incorporated by reference in their entirety.

One particular hypersensitive response elicitor protein, known as harpin$_{Ea}$, is commercially available from Eden Bioscience Corporation (Bothell, Wash.) under the name of Messenger®. Messenger contains 3% by weight of harpin$_{Ea}$ as the active ingredient and 97% by weight inert ingredients. Harpin$_{Ea}$ is one type of hypersensitive response elicitor protein from *Erwinia amylovora*. Harpin$_{Ea}$ has an amino acid sequence corresponding to SEQ. ID. No. 3 as follows:

```
Met Ser Leu Asn Thr Ser Gly Leu Gly Ala Ser Thr Met Gln Ile Ser
1               5                   10                  15

Ile Gly Gly Ala Gly Gly Asn Asn Gly Leu Leu Gly Thr Ser Arg Gln
                20                  25                  30

Asn Ala Gly Leu Gly Gly Asn Ser Ala Leu Gly Leu Gly Gly Gly Asn
                35                  40                  45

Gln Asn Asp Thr Val Asn Gln Leu Ala Gly Leu Leu Thr Gly Met Met
            50                  55                  60

Met Met Met Ser Met Met Gly Gly Gly Leu Met Gly Gly Gly Leu
65                  70                  75                  80

Gly Gly Gly Leu Gly Asn Gly Leu Gly Gly Ser Gly Gly Leu Gly Glu
                85                  90                  95

Gly Leu Ser Asn Ala Leu Asn Asp Met Leu Gly Gly Ser Leu Asn Thr
                100                 105                 110

Leu Gly Ser Lys Gly Gly Asn Asn Thr Thr Ser Thr Thr Asn Ser Pro
            115                 120                 125

Leu Asp Gln Ala Leu Gly Ile Asn Ser Thr Ser Gln Asn Asp Asp Ser
        130                 135                 140

Thr Ser Gly Thr Asp Ser Thr Ser Asp Ser Ser Asp Pro Met Gln Gln
145                 150                 155                 160

Leu Leu Lys Met Phe Ser Glu Ile Met Gln Ser Leu Phe Gly Asp Gly
                165                 170                 175

Gln Asp Gly Thr Gln Gly Ser Ser Ser Gly Gly Lys Gln Pro Thr Glu
            180                 185                 190

Gly Glu Gln Asn Ala Tyr Lys Lys Gly Val Thr Asp Ala Leu Ser Gly
            195                 200                 205

Leu Met Gly Asn Gly Leu Ser Gln Leu Leu Gly Asn Gly Gly Leu Gly
```

-continued

```
            210                 215                 220
Gly Gly Gln Gly Gly Asn Ala Gly Thr Gly Leu Asp Gly Ser Ser Leu
225                 230                 235                 240

Gly Gly Lys Gly Leu Gln Asn Leu Ser Gly Pro Val Asp Tyr Gln Gln
                245                 250                 255

Leu Gly Asn Ala Val Gly Thr Gly Ile Gly Met Lys Ala Gly Ile Gln
                260                 265                 270

Ala Leu Asn Asp Ile Gly Thr His Arg His Ser Ser Thr Arg Ser Phe
            275                 280                 285

Val Asn Lys Gly Asp Arg Ala Met Ala Lys Glu Ile Gly Gln Phe Met
        290                 295                 300

Asp Gln Tyr Pro Glu Val Phe Gly Lys Pro Gln Tyr Gln Lys Gly Pro
305                 310                 315                 320

Gly Gln Glu Val Lys Thr Asp Asp Lys Ser Trp Ala Lys Ala Leu Ser
                325                 330                 335

Lys Pro Asp Asp Asp Gly Met Thr Pro Ala Ser Met Glu Gln Phe Asn
                340                 345                 350

Lys Ala Lys Gly Met Ile Lys Arg Pro Met Ala Gly Asp Thr Gly Asn
            355                 360                 365

Gly Asn Leu Gln Ala Arg Gly Ala Gly Gly Ser Ser Leu Gly Ile Asp
        370                 375                 380

Ala Met Met Ala Gly Asp Ala Ile Asn Asn Met Ala Leu Gly Lys Leu
385                 390                 395                 400

Gly Ala Ala
```

This hypersensitive response elicitor protein or polypeptide has a molecular weight of about 39 kDa, has a pI of approximately 4.3, and is heat stable at 100° C. for at least 10 minutes. This hypersensitive response elicitor protein or polypeptide has substantially no cysteine. The hypersensitive response elicitor protein or polypeptide derived from *Erwinia amylovora* is more fully described in Wei, Z-M., et al., "Harpin, Elicitor of the Hypersensitive Response Produced by the Plant Pathogen *Erwinia amylovora*," *Science* 257:85-88 (1992), which is hereby incorporated by reference in its entirety. The DNA molecule encoding this hypersensitive response elicitor protein or polypeptide has a nucleotide sequence corresponding to SEQ. ID. No. 4 as follows:

```
aagcttcggc atggcacgtt tgaccgttgg gtcggcaggg tacgtttgaa ttattcataa   60
gaggaatacg ttatgagtct gaatacaagt gggctgggag cgtcaacgat gcaaatttct  120
atcggcggtg cgggcggaaa taacgggttg ctgggtacca gtcgccagaa tgctgggttg  180
ggtggcaatt ctgcactggg gctgggcggc ggtaatcaaa atgataccgt caatcagctg  240
gctggcttac tcaccggcat gatgatgatg atgagcatga tgggcggtgg tgggctgatg  300
ggcggtggct taggcggtgg cttaggtaat ggcttgggtg gctcaggtgg cctgggcgaa  360
ggactgtcga acgcgctgaa cgatatgtta ggcggttcgc tgaacacgct gggctcgaaa  420
ggcggcaaca ataccacttc aacaacaaat tccccgctgg accaggcgct gggtattaac  480
tcaacgtccc aaaacgacga ttccacctcc ggcacagatt ccacctcaga ctccagcgac  540
ccgatgcagc agctgctgaa gatgttcagc gagataatgc aaagcctgtt tggtgatggg  600
caagatggca cccagggcag ttcctctggg ggcaagcagc cgaccgaagg cgagcagaac  660
gcctataaaa aaggagtcac tgatgcgctg tcgggcctga tgggtaatgg tctgagccag  720
ctccttggca acggggggact gggaggtggt cagggcggta atgctggcac gggtcttgac  780
ggttcgtcgc tgggcggcaa agggctgcaa aacctgagcg gccggtgga ctaccagcag  840
ttaggtaacg ccgtgggtac cggtatcggt atgaaagcgg gcattcaggc gctgaatgat  900
atcggtacgc acaggcacag ttcaacccgt tctttcgtca ataaaggcga tcgggcgatg  960
```

-continued

```
gcgaaggaaa tcggtcagtt catggaccag tatcctgagg tgtttggcaa gccgcagtac 1020
cagaaaggcc cgggtcagga ggtgaaaacc gatgacaaat catgggcaaa agcactgagc 1080
aagccagatg acgacggaat gacaccagcc agtatggagc agttcaacaa agccaagggc 1140
atgatcaaaa ggcccatggc gggtgatacc ggcaacggca acctgcaggc acgcggtgcc 1200
ggtggttctt cgctgggtat tgatgccatg atggccggtg atgccattaa caatatggca 1260
cttggcaagc tgggcgcggc ttaagctt                                    1288
```

The above nucleotide and amino acid sequences are disclosed and further described in U.S. Pat. No. 5,849,868 to Beer et al. and U.S. Pat. No. 5,776,889 to Wei et al., which are hereby incorporated by reference in their entirety.

Another hypersensitive response elicitor protein or polypeptide derived from *Erwinia amylovora* has an amino acid sequence corresponding to SEQ. ID. No. 5 as follows:

```
Met Ser Ile Leu Thr Leu Asn Asn Asn Thr Ser Ser Ser Pro Gly Leu
1               5                   10                  15

Phe Gln Ser Gly Gly Asp Asn Gly Leu Gly Gly His Asn Ala Asn Ser
            20                  25                  30

Ala Leu Gly Gln Gln Pro Ile Asp Arg Gln Thr Ile Glu Gln Met Ala
        35                  40                  45

Gln Leu Leu Ala Glu Leu Leu Lys Ser Leu Leu Ser Pro Gln Ser Gly
    50                  55                  60

Asn Ala Ala Thr Gly Ala Gly Gly Asn Asp Gln Thr Thr Gly Val Gly
65                  70                  75                  80

Asn Ala Gly Gly Leu Asn Gly Arg Lys Gly Thr Ala Gly Thr Thr Pro
                85                  90                  95

Gln Ser Asp Ser Gln Asn Met Leu Ser Glu Met Gly Asn Asn Gly Leu
            100                 105                 110

Asp Gln Ala Ile Thr Pro Asp Gly Gln Gly Gly Gly Gln Ile Gly Asp
        115                 120                 125

Asn Pro Leu Leu Lys Ala Met Leu Lys Leu Ile Ala Arg Met Met Asp
    130                 135                 140

Gly Gln Ser Asp Gln Phe Gly Gln Pro Gly Thr Gly Asn Asn Ser Ala
145                 150                 155                 160

Ser Ser Gly Thr Ser Ser Ser Gly Gly Ser Pro Phe Asn Asp Leu Ser
                165                 170                 175

Gly Gly Lys Ala Pro Ser Gly Asn Ser Pro Ser Gly Asn Tyr Ser Pro
            180                 185                 190

Val Ser Thr Phe Ser Pro Pro Ser Thr Pro Thr Ser Pro Thr Ser Pro
        195                 200                 205

Leu Asp Phe Pro Ser Ser Pro Thr Lys Ala Ala Gly Gly Ser Thr Pro
    210                 215                 220

Val Thr Asp His Pro Asp Pro Val Gly Ser Ala Gly Ile Gly Ala Gly
225                 230                 235                 240

Asn Ser Val Ala Phe Thr Ser Ala Gly Ala Asn Gln Thr Val Leu His
                245                 250                 255

Asp Thr Ile Thr Val Lys Ala Gly Gln Val Phe Asp Gly Lys Gly Gln
            260                 265                 270

Thr Phe Thr Ala Gly Ser Glu Leu Gly Asp Gly Gly Gln Ser Glu Asn
        275                 280                 285

Gln Lys Pro Leu Phe Ile Leu Glu Asp Gly Ala Ser Leu Lys Asn Val
    290                 295                 300

Thr Met Gly Asp Asp Gly Ala Asp Gly Ile His Leu Tyr Gly Asp Ala
305                 310                 315                 320

Lys Ile Asp Asn Leu His Val Thr Asn Val Gly Glu Asp Ala Ile Thr
```

-continued

```
                     325                 330                 335
Val Lys Pro Asn Ser Ala Gly Lys Lys Ser His Val Glu Ile Thr Asn
                340                 345                 350

Ser Ser Phe Glu His Ala Ser Asp Lys Ile Leu Gln Leu Asn Ala Asp
            355                 360                 365

Thr Asn Leu Ser Val Asp Asn Val Lys Ala Lys Asp Phe Gly Thr Phe
        370                 375                 380

Val Arg Thr Asn Gly Gly Gln Gln Gly Asn Trp Asp Leu Asn Leu Ser
385                 390                 395                 400

His Ile Ser Ala Glu Asp Gly Lys Phe Ser Phe Val Lys Ser Asp Ser
                405                 410                 415

Glu Gly Leu Asn Val Asn Thr Ser Asp Ile Ser Leu Gly Asp Val Glu
                420                 425                 430

Asn His Tyr Lys Val Pro Met Ser Ala Asn Leu Lys Val Ala Glu
            435                 440                 445
```

This protein or polypeptide is acidic, rich in glycine and serine, and lacks cysteine. It is also heat stable, protease sensitive, and suppressed by inhibitors of plant metabolism. The protein or polypeptide of the present invention has a predicted molecular size of ca. 45 kDa. The DNA molecule encoding this hypersensitive response elicitor protein or polypeptide has a nucleotide sequence corresponding to SEQ. ID. No. 6 as follows:

The above nucleotide and amino acid sequences are disclosed and further described in PCT Application Publication No. WO 99/07208 to Kim et al., which is hereby incorporated by reference in its entirety.

A hypersensitive response elicitor protein or polypeptide derived from *Pseudomonas syringae* has an amino acid sequence corresponding to SEQ. ID. No. 7 as follows:

```
atgtcaattc ttacgcttaa caacaatacc tcgtcctcgc cgggtctgtt ccagtccggg    60
ggggacaacg ggcttggtgg tcataatgca aattctgcgt tggggcaaca acccatcgat   120
cggcaaacca ttgagcaaat ggctcaatta ttggcggaac tgttaaagtc actgctatcg   180
ccacaatcag gtaatgcggc aaccggagcc ggtggcaatg accagactac aggagttggt   240
aacgctggcg gcctgaacgg acgaaaaggc acagcaggaa ccactccgca gtctgacagt   300
cagaacatgc tgagtgagat gggcaacaac gggctggatc aggccatcac gcccgatggc   360
cagggcggcg gcagatcgg cgataatcct ttactgaaag ccatgctgaa gcttattgca   420
cgcatgatgg acggccaaag cgatcagttt ggccaacctg gtacgggcaa caacagtgcc   480
tcttccggta cttcttcatc tggcggttcc ccttttaacg atctatcagg ggggaaggcc   540
ccttccggca actccccttc cggcaactac tctcccgtca gtaccttctc acccccatcc   600
acgccaacgt cccctacctc accgcttgat ttcccttctt ctcccaccaa agcagccggg   660
ggcagcacgc cggtaaccga tcatcctgac cctgttggta gcgcgggcat cggggccgga   720
aattcggtgg ccttcaccag cgccggcgct aatcagacgg tgctgcatga caccattacc   780
gtgaaagcgg gtcaggtgtt tgatggcaaa ggacaaacct tcaccgccgg ttcagaatta   840
ggcgatggcg gccagtctga aaaccagaaa ccgctgttta tactggaaga cggtgccagc   900
ctgaaaaacg tcaccatggg cgacgacggg gcggatggta ttcatcttta cggtgatgcc   960
aaaatagaca atctgcacgt caccaacgtg ggtgaggacg cgattaccgt taagccaaac  1020
agcgcgggca aaaatccca cgttgaaatc actaacagtt ccttcgagca cgcctctgac  1080
aagatcctgc agctgaatgc cgatactaac ctgagcgttg acaacgtgaa ggccaaagac  1140
tttggtactt ttgtacgcac taacggcggt caacagggta actgggatct gaatctgagc  1200
catatcagcg cagaagacgg taagttctcg ttcgttaaaa gcgatagcga ggggctaaac  1260
gtcaatacca gtgatatctc actgggtgat gttgaaaacc actacaaagt gccgatgtcc  1320
gccaacctga aggtggctga atga                                        1344
```

```
Met Gln Ser Leu Ser Leu Asn Ser Ser Ser Leu Gln Thr Pro Ala Met
1               5                   10                  15

Ala Leu Val Leu Val Arg Pro Glu Ala Glu Thr Thr Gly Ser Thr Ser
            20                  25              30

Ser Lys Ala Leu Gln Glu Val Val Lys Leu Ala Glu Glu Leu Met
        35                  40              45

Arg Asn Gly Gln Leu Asp Asp Ser Ser Pro Leu Gly Lys Leu Leu Ala
    50              55                  60

Lys Ser Met Ala Ala Asp Gly Lys Ala Gly Gly Ile Glu Asp Val
65              70              75                      80

Ile Ala Ala Leu Asp Lys Leu Ile His Glu Lys Leu Gly Asp Asn Phe
            85              90                  95

Gly Ala Ser Ala Asp Ser Ala Ser Gly Thr Gly Gln Gln Asp Leu Met
            100             105             110

Thr Gln Val Leu Asn Gly Leu Ala Lys Ser Met Leu Asp Asp Leu Leu
        115             120             125

Thr Lys Gln Asp Gly Gly Thr Ser Phe Ser Glu Asp Asp Met Pro Met
    130             135             140

Leu Asn Lys Ile Ala Gln Phe Met Asp Asn Pro Ala Gln Phe Pro
145             150             155             160

Lys Pro Asp Ser Gly Ser Trp Val Asn Glu Leu Lys Glu Asp Asn Phe
            165             170             175

Leu Asp Gly Asp Glu Thr Ala Ala Phe Arg Ser Ala Leu Asp Ile Ile
            180             185             190

Gly Gln Gln Leu Gly Asn Gln Gln Ser Asp Ala Gly Ser Leu Ala Gly
        195             200             205

Thr Gly Gly Gly Leu Gly Thr Pro Ser Ser Phe Ser Asn Asn Ser Ser
    210             215             220

Val Met Gly Asp Pro Leu Ile Asp Ala Asn Thr Gly Pro Gly Asp Ser
225             230             235             240

Gly Asn Thr Arg Gly Glu Ala Gly Gln Leu Ile Gly Glu Leu Ile Asp
            245             250             255

Arg Gly Leu Gln Ser Val Leu Ala Gly Gly Gly Leu Gly Thr Pro Val
            260             265             270

Asn Thr Pro Gln Thr Gly Thr Ser Ala Asn Gly Gly Gln Ser Ala Gln
        275             280             285

Asp Leu Asp Gln Leu Leu Gly Gly Leu Leu Leu Lys Gly Leu Glu Ala
        290             295             300

Thr Leu Lys Asp Ala Gly Gln Thr Gly Thr Asp Val Gln Ser Ser Ala
305             310             315             320

Ala Gln Ile Ala Thr Leu Leu Val Ser Thr Leu Leu Gln Gly Thr Arg
                325             330             335

Asn Gln Ala Ala Ala
            340
```

This hypersensitive response elicitor protein or polypeptide has a molecular weight of 34-35 kDa. It is rich in glycine (about 13.5%) and lacks cysteine and tyrosine. Further information about the hypersensitive response elicitor derived from *Pseudomonas syringae* is found in He, S. Y., et al., "*Pseudomonas syringae* pv. *syringae* Harpin$_{Pss}$: a Protein that is Secreted via the Hrp Pathway and Elicits the Hypersensitive Response in Plants," *Cell* 73:1255-1266 (1993), which is hereby incorporated by reference in its entirety. The DNA molecule encoding this hypersensitive response elicitor from *Pseudomonas syringae* has a nucleotide sequence corresponding to SEQ. ID. No. 8 as follows:

```
atgcagagtc tcagtcttaa cagcagctcg ctgcaaaccc cggcaatggc ccttgtcctg   60
gtacgtcctg aagccgagac gactggcagt acgtcgagca aggcgcttca ggaagttgtc  120
```

-continued

```
gtgaagctgg ccgaggaact gatgcgcaat ggtcaactcg acgacagctc gccattggga  180
aaactgttgg ccaagtcgat ggccgcagat ggcaaggcgg gcggcggtat tgaggatgtc  240
atcgctgcgc tggacaagct gatccatgaa aagctcggtg acaacttcgg cgcgtctgcg  300
gacagcgcct cgggtaccgg acagcaggac ctgatgactc aggtgctcaa tggcctggcc  360
aagtcgatgc tcgatgatct tctgaccaag caggatggcg ggacaagctt ctccgaagac  420
gatatgccga tgctgaacaa gatcgcgcag ttcatggatg acaatcccgc acagtttccc  480
aagccggact cgggctcctg ggtgaacgaa ctcaaggaag acaacttcct tgatggcgac  540
gaaacggctg cgttccgttc ggcactcgac atcattggcc agcaactggg taatcagcag  600
agtgacgctg gcagtctggc agggacgggt ggaggtctgg gcactccgag cagttttttcc  660 aacaactcgt ccgtgatggg tgatccgctg atcgacgcca ataccggtcc cggtgacagc  720
ggcaataccc gtggtgaagc ggggcaactg atcggcgagc ttatcgaccg tggcctgcaa  780
tcggtattgg ccggtggtgg actgggcaca cccgtaaaca ccccgcagac cggtacgtcg  840
gcgaatggcg gacagtccgc tcaggatctt gatcagttgc tgggcggctt gctgctcaag  900
ggcctggagg caacgctcaa ggatgccggg caaacaggca ccgacgtgca gtcgagcgct  960
gcgcaaatcg ccaccttgct ggtcagtacg ctgctgcaag gcacccgcaa tcaggctgca 1020
gcctga                                                           1026
```

The above nucleotide and amino acid sequences are disclosed and further described in U.S. Pat. No. 5,708,139 to Collmer et al. and U.S. Pat. No. 5,776,889 to Wei et al., which are hereby incorporated by reference in their entirety.

Another hypersensitive response elicitor protein or polypeptide derived from *Pseudomonas syringae* has an amino acid sequence corresponding to SEQ. ID. No. 9 as follows:

```
Met Ser Ile Gly Ile Thr Pro Arg Pro Gln Thr Thr Thr Pro Leu
1               5                   10                  15

Asp Phe Ser Ala Leu Ser Gly Lys Ser Pro Gln Pro Asn Thr Phe Gly
            20                  25                  30

Glu Gln Asn Thr Gln Gln Ala Ile Asp Pro Ser Ala Leu Leu Phe Gly
                35                  40                  45

Ser Asp Thr Gln Lys Asp Val Asn Phe Gly Thr Pro Asp Ser Thr Val
        50                  55                  60

Gln Asn Pro Gln Asp Ala Ser Lys Pro Asn Asp Ser Gln Ser Asn Ile
65                  70                  75                  80

Ala Lys Leu Ile Ser Ala Leu Ile Met Ser Leu Leu Gln Met Leu Thr
                85                  90                  95

Asn Ser Asn Lys Lys Gln Asp Thr Asn Gln Glu Gln Pro Asp Ser Gln
            100                 105                 110

Ala Pro Phe Gln Asn Asn Gly Gly Leu Gly Thr Pro Ser Ala Asp Ser
                115                 120                 125

Gly Gly Gly Gly Thr Pro Asp Ala Thr Gly Gly Gly Gly Asp Thr
        130                 135                 140

Pro Ser Ala Thr Gly Gly Gly Gly Asp Thr Pro Thr Ala Thr Gly
145                 150                 155                 160

Gly Gly Gly Ser Gly Gly Gly Gly Thr Pro Thr Ala Thr Gly Gly Gly
                165                 170                 175

Ser Gly Gly Thr Pro Thr Ala Thr Gly Gly Gly Glu Gly Val Thr
            180                 185                 190

Pro Gln Ile Thr Pro Gln Leu Ala Asn Pro Asn Arg Thr Ser Gly Thr
            195                 200                 205

Gly Ser Val Ser Asp Thr Ala Gly Ser Thr Glu Gln Ala Gly Lys Ile
            210                 215                 220
```

```
Asn Val Val Lys Asp Thr Ile Lys Val Gly Ala Gly Glu Val Phe Asp
225                 230                 235                 240
Gly His Gly Ala Thr Phe Thr Ala Asp Lys Ser Met Gly Asn Gly Asp
                245                 250                 255
Gln Gly Glu Asn Gln Lys Pro Met Phe Glu Leu Ala Glu Gly Ala Thr
            260                 265                 270
Leu Lys Asn Val Asn Leu Gly Glu Asn Glu Val Asp Gly Ile His Val
        275                 280                 285
Lys Ala Lys Asn Ala Gln Glu Val Thr Ile Asp Asn Val His Ala Gln
    290                 295                 300
Asn Val Gly Glu Asp Leu Ile Thr Val Lys Gly Glu Gly Gly Ala Ala
305                 310                 315                 320
Val Thr Asn Leu Asn Ile Lys Asn Ser Ser Ala Lys Gly Ala Asp Asp
                325                 330                 335
Lys Val Val Gln Leu Asn Ala Asn Thr His Leu Lys Ile Asp Asn Phe
            340                 345                 350
Lys Ala Asp Asp Phe Gly Thr Met Val Arg Thr Asn Gly Gly Lys Gln
        355                 360                 365
Phe Asp Asp Met Ser Ile Glu Leu Asn Gly Ile Glu Ala Asn His Gly
    370                 375                 380
Lys Phe Ala Leu Val Lys Ser Asp Ser Asp Asp Leu Lys Leu Ala Thr
385                 390                 395                 400
Gly Asn Ile Ala Met Thr Asp Val Lys His Ala Tyr Asp Lys Thr Gln
                405                 410                 415
Ala Ser Thr Gln His Thr Glu Leu
            420
```

This protein or polypeptide is acidic, glycine-rich, lacks cysteine, and is deficient in aromatic amino acids. The DNA molecule encoding this hypersensitive response elicitor from *Pseudomonas syringae* has a nucleotide sequence corresponding to SEQ. ID. No. 10 as follows:

```
tccacttcgc tgattttgaa attggcagat tcatagaaac gttcaggtgt ggaaatcagg   60
ctgagtgcgc agatttcgtt gataagggtg tggtactggt cattgttggt catttcaagg  120
cctctgagtg cggtgcggag caataccagt cttcctgctg gcgtgtgcac actgagtcgc  180
aggcataggc atttcagttc cttgcgttgg ttgggcatat aaaaaaagga acttttaaaa  240
acagtgcaat gagatgccgg caaaacggga accggtcgct gcgctttgcc actcacttcg  300
agcaagctca accccaaaca tccacatccc tatcgaacgg acagcgatac ggccacttgc  360
tctggtaaac cctggagctg gcgtcggtcc aattgcccac ttagcgaggt aacgcagcat  420
gagcatcggc atcacacccc ggccgcaaca gaccaccacg ccactcgatt tttcggcgct  480
aagcggcaag agtcctcaac caaacacgtt cggcgagcag aacactcagc aagcgatcga  540
cccgagtgca ctgttgttcg gcagcgacac acagaaagac gtcaacttcg gcacgcccga  600
cagcaccgtc cagaatccgc aggacgccag caagcccaac gacagccagt ccaacatcgc  660
taaattgatc agtgcattga tcatgtcgtt gctgcagatg ctcaccaact ccaataaaaa  720
gcaggacacc aatcaggaac agcctgatag ccaggctcct ttccagaaca acggcgggct  780
cggtacaccg tcggccgata gcgggggcgg cggtacaccg gatgcgacag gtggcggcgg  840
cggtgatacg ccaagcgcaa caggcggtgg cggcggtgat actccgaccg caacaggcgg  900
tggcggcagc ggtggcggcg gcacacccac tgcaacaggt ggcggcagcg gtggcacacc  960
```

```
                                    -continued
cactgcaaca ggcggtggcg agggtggcgt aacaccgcaa atcactccgc agttggccaa 1020
ccctaaccgt acctcaggta ctggctcggt gtcggacacc gcaggttcta ccgagcaagc 1080
cggcaagatc aatgtggtga agacaccat caaggtcggc gctggcgaag tctttgacgg 1140
ccacggcgca accttcactg ccgacaaatc tatgggtaac ggagaccagg gcgaaaatca 1200
gaagcccatg ttcgagctgg ctgaaggcgc tacgttgaag aatgtgaacc tgggtgagaa 1260
cgaggtcgat ggcatccacg tgaaagccaa aaacgctcag gaagtcacca ttgacaacgt 1320
gcatgcccag aacgtcggtg aagacctgat tacggtcaaa ggcgagggag gcgcagcggt 1380
cactaatctg aacatcaaga acagcagtgc caaggtgca gacgacaagg ttgtccagct 1440
caacgccaac actcacttga aaatcgacaa cttcaaggcc gacgatttcg gcacgatggt 1500
tcgcaccaac ggtggcaagc agtttgatga catgagcatc gagctgaacg gcatcgaagc 1560
taaccacggc aagttcgccc tggtgaaaag cgacagtgac gatctgaagc tggcaacggg 1620
caacatcgcc atgaccgacg tcaaacacgc ctacgataaa acccaggcat cgacccaaca 1680
caccgagctt tgaatccaga caagtagctt gaaaaaaggg ggtggactc              1729
```

The above nucleotide and amino acid sequences are disclosed and further described in U.S. Pat. No. 6,172,184 to Collmer et al., which is hereby incorporated by reference in its entirety.

A hypersensitive response elicitor protein or polypeptide derived from *Pseudomonas solanacearum* has an amino acid sequence corresponding to SEQ. ID. No. 11 as follows:

```
Met Ser Val Gly Asn Ile Gln Ser Pro Ser Asn Leu Pro Gly Leu Gln
1               5                   10                  15

Asn Leu Asn Leu Asn Thr Asn Thr Asn Ser Gln Gln Ser Gly Gln Ser
            20                  25                  30

Val Gln Asp Leu Ile Lys Gln Val Glu Lys Asp Ile Leu Asn Ile Ile
        35                  40                  45

Ala Ala Leu Val Gln Lys Ala Ala Gln Ser Ala Gly Gly Asn Thr Gly
    50                  55                  60

Asn Thr Gly Asn Ala Pro Ala Lys Asp Gly Asn Ala Asn Ala Gly Ala
65                  70                  75                  80

Asn Asp Pro Ser Lys Asn Asp Pro Ser Lys Ser Gln Ala Pro Gln Ser
                85                  90                  95

Ala Asn Lys Thr Gly Asn Val Asp Asp Ala Asn Asn Gln Asp Pro Met
            100                 105                 110

Gln Ala Leu Met Gln Leu Leu Glu Asp Leu Val Lys Leu Leu Lys Ala
        115                 120                 125

Ala Leu His Met Gln Gln Pro Gly Gly Asn Asp Lys Gly Asn Gly Val
    130                 135                 140

Gly Gly Ala Asn Gly Ala Lys Gly Ala Gly Gly Gln Gly Gly Leu Ala
145                 150                 155                 160

Glu Ala Leu Gln Glu Ile Glu Gln Ile Leu Ala Gln Leu Gly Gly Gly
                165                 170                 175

Gly Ala Gly Ala Gly Gly Ala Gly Gly Gly Val Gly Gly Ala Gly Gly
            180                 185                 190

Ala Asp Gly Gly Ser Gly Ala Gly Gly Ala Gly Gly Ala Asn Gly Ala
        195                 200                 205

Asp Gly Gly Asn Gly Val Asn Gly Asn Gln Ala Asn Gly Pro Gln Asn
    210                 215                 220

Ala Gly Asp Val Asn Gly Ala Asn Gly Ala Asp Asp Gly Ser Glu Asp
225                 230                 235                 240

Gln Gly Gly Leu Thr Gly Val Leu Gln Lys Leu Met Lys Ile Leu Asn
                245                 250                 255
```

```
Ala Leu Val Gln Met Met Gln Gln Gly Gly Leu Gly Gly Asn Gln
            260             265             270

Ala Gln Gly Gly Ser Lys Gly Ala Gly Asn Ala Ser Pro Ala Ser Gly
        275             280             285

Ala Asn Pro Gly Ala Asn Gln Pro Gly Ser Ala Asp Asp Gln Ser Ser
    290             295             300

Gly Gln Asn Asn Leu Gln Ser Gln Ile Met Asp Val Val Lys Glu Val
305             310             315             320

Val Gln Ile Leu Gln Gln Met Leu Ala Ala Gln Asn Gly Gly Ser Gln
            325             330             335

Gln Ser Thr Ser Thr Gln Pro Met
            340
```

Further information regarding this hypersensitive response elicitor protein or polypeptide derived from *Pseudomonas solanacearum* is set forth in Arlat, M., et al., "PopA1, a Protein which Induces a Hypersensitive-like Response in Specific Petunia Genotypes, is Secreted via the Hrp Pathway of *Pseudomonas solanacearum*," EMBO J. 13:543-533 (1994), which is hereby incorporated by reference in its entirety. It is encoded by a DNA molecule from *Pseudomonas solanacearum* having a nucleotide sequence corresponding SEQ. ID. No. 12 as follows:

```
atgtcagtcg gaaacatcca gagcccgtcg aacctcccgg gtctgcagaa cctgaacctc    60
aacaccaaca ccaacagcca gcaatcgggc cagtccgtgc aagacctgat caagcaggtc   120
gagaaggaca tcctcaacat catcgcagcc ctcgtgcaga aggccgcaca gtcggcgggc   180
ggcaacaccg gtaacaccgg caacgcgccg gcgaaggacg gcaatgccaa cgcgggcgcc   240
aacgacccga gcaagaacga cccgagcaag agccaggctc cgcagtcggc caacaagacc   300
ggcaacgtcg acgacgccaa caaccaggat ccgatgcaag cgctgatgca gctgctggaa   360
gacctggtga agctgctgaa ggcggccctg cacatgcagc agcccggcgg caatgacaag   420
ggcaacggcg tgggcggtgc caacggcgcc aagggtgccg gcggccaggg cggcctggcc   480
gaagcgctgc aggagatcga gcagatcctc gcccagctcg gcggcggcgg tgctggcgcc   540
ggcggcgcgg gtggcggtgt cggcggtgct ggtggcgcgg atggcggctc cggtgcgggt   600
ggcgcaggcg gtgcgaacgg cgccgacggc ggcaatggcg tgaacggcaa ccaggcgaac   660
ggcccgcaga acgcaggcga tgtcaacggt gccaacggcg cggatgacgg cagcgaagac   720
cagggcggcc tcaccggcgt gctgcaaaag ctgatgaaga tcctgaacgc gctggtgcag   780
atgatgcagc aaggcggcct cggcggcggc aaccaggcgc agggcggctc gaagggtgcc   840
ggcaacgcct cgccggcttc cggcgcgaac ccgggcgcga accagcccgg ttcggcggat   900
gatcaatcgt ccggccagaa caatctgcaa tcccagatca tggatgtggt gaaggaggtc   960
gtccagatcc tgcagcagat gctggcggcg cagaacggcg gcagccagca gtccacctcg  1020
acgcagccga tgtaa                                                    1035
```

The above nucleotide and amino acid sequences are disclosed and further described in U.S. Pat. No. 5,776,889 to Wei et al., which is hereby incorporated by reference in its entirety.

A hypersensitive response elicitor polypeptide or protein derived from *Xanthomonas campestris* has an amino acid sequence corresponding to SEQ. ID. No. 13 as follows:

```
Met Asp Ser Ile Gly Asn Asn Phe Ser Asn Ile Gly Asn Leu Gln Thr
1               5                   10                  15

Met Gly Ile Gly Pro Gln Gln His Glu Asp Ser Ser Gln Ser Pro
                20                  25                  30

Ser Ala Gly Ser Glu Gln Gln Leu Asp Gln Leu Leu Ala Met Phe Ile
```

-continued

```
                35                  40                  45
Met Met Met Leu Gln Gln Ser Gln Gly Ser Asp Ala Asn Gln Glu Cys
        50                  55                  60

Gly Asn Glu Gln Pro Gln Asn Gly Gln Gln Glu Gly Leu Ser Pro Leu
65                  70                  75                  80

Thr Gln Met Leu Met Gln Ile Val Met Gln Leu Met Gln Asn Gln Gly
                85                  90                  95

Gly Ala Gly Met Gly Gly Gly Gly Ser Val Asn Ser Ser Leu Gly Gly
            100                 105                 110

Asn Ala
```

This hypersensitive response elicitor polypeptide or protein has an estimated molecular weight of about 12 kDa based on the deduced amino acid sequence, which is consistent with a molecular weight of about 14 kDa as detected by SDS-PAGE. The above protein or polypeptide is encoded by a DNA molecule according to SEQ. ID. No. 14 as follows:

```
atggactcta tcggaaacaa cttttcgaat atcggcaacc tgcagacgat gggcatcggg  60
cctcagcaac acgaggactc cagccagcag tcgccttcgg ctggctccga gcagcagctg  120
gatcagttgc tcgccatgtt catcatgatg atgctgcaac agagccaggg cagcgatgca  180
aatcaggagt gtggcaacga acaaccgcag aacggtcaac aggaaggcct gagtccgttg  240
acgcagatgc tgatgcagat cgtgatgcag ctgatgcaga accagggcgg cgccggcatg  300
ggcggtggcg gttcggtcaa cagcagcctg ggcggcaacg cc                     342
```

The above nucleotide and amino acid sequences are disclosed and further described in U.S. patent application Ser. No. 09/829,124, which is hereby incorporated by reference in its entirety.

Other embodiments of the present invention include, but are not limited to, use of a hypersensitive response elicitor protein or polypeptide derived from *Erwinia carotovora* and *Erwinia stewartii*. Isolation of *Erwinia carotovora* hypersensitive response elicitor protein or polypeptide is described in Cui, et al., "The RsmA Mutants of *Erwinia carotovora* subsp. *carotovora* Strain Ecc7 Overexpress hrp $N_{Ecc}$ and Elicit a Hypersensitive Reaction-like Response in Tobacco Leaves," *MPMI*, 9(7):565-73 (1996), which is hereby incorporated by reference in its entirety. A hypersensitive response elicitor protein or polypeptide of *Erwinia stewartii* is set forth in Ahmad, et al., "Harpin is Not Necessary for the Pathogenicity of *Erwinia stewartii* on Maize," 8*th Int'l. Cone. Molec. Plant-Microbe Interact.*, Jul. 14-19, 1996 and Ahmad, et al., "Harpin is Not Necessary for the Pathogenicity of *Erwinia stewartii* on Maize," *Ann. Mtg. Am. Phytopath. Soc.*, Jul. 27-31, 1996, which are hereby incorporated by reference in their entirety.

Other elicitors can be readily identified by isolating putative hypersensitive response elicitors and testing them for elicitor activity as described, for example, in Wei, Z-M., et al., "Harpin, Elicitor of the Hypersensitive Response Produced by the Plant Pathogen *Erwinia amylovora*," *Science* 257:85-88 (1992), which is hereby incorporated by reference in its entirety. Cell-free preparations from culture supernatants can be tested for elicitor activity (i.e., local necrosis) by using them to infiltrate appropriate plant tissues. Once identified, DNA molecules encoding a hypersensitive response elicitor can be isolated using standard techniques known to those skilled in the art.

The hypersensitive response elicitor protein or polypeptide can also be a fragment of the above referenced hypersensitive response elicitor proteins or polypeptides as well as fragments of full length elicitors from other pathogens.

Suitable fragments can be produced by several means. Subclones of the gene encoding a known elicitor protein can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (1989), and Ausubel et al. (ed.), *Current Protocols in Molecular Biology*, John Wiley & Sons (New York, N.Y.) (1999 and preceding editions), which are hereby incorporated by reference in their entirety. The subolones then are expressed in vitro or in vivo in bacterial cells to yield a smaller protein or polypeptide that can be tested for elicitor activity, e.g., using procedures set forth in Wei, Z-M., et al., *Science* 257: 85-88 (1992), which is hereby incorporated by reference in its entirety.

In another approach, based on knowledge of the primary structure of the protein, fragments of the elicitor protein gene may be synthesized using the PCR technique together with specific sets of primers chosen to represent particular portions of the protein. Erlich, H. A., et al., "Recent Advances in the Polymerase Chain Reaction," *Science* 252:1643-51 (1991), which is hereby incorporated by reference in its entirety. These can then be cloned into an appropriate vector for expression of a truncated protein or polypeptide from bacterial cells as described above.

Examples of suitable fragments of a hypersensitive response elicitor are described in WIPO International Publication Numbers: WO 98/54214 and WO 01/98501, which are hereby incorporated by reference in their entirety.

DNA molecules encoding a hypersensitive response elicitor protein or polypeptide can also include a DNA molecule that hybridizes under stringent conditions to the DNA molecule having a nucleotide sequences from one of the above identified hypersensitive response licitors. An example of suitable stringency conditions is when hybridization is carried out at a temperature of about 37° C. using a hybridization medium that includes 0.9M sodium citrate ("SSC") buffer, followed by washing with 0.2×SSC buffer at 37° C. Higher stringency can readily be attained by increasing the temperature for either hybridization or washing conditions or increasing the sodium concentration of the hybridization or wash medium. Nonspecific binding may also be controlled using any one of a number of known techniques such as, for example, blocking the membrane with protein-containing solutions, addition of heterologous RNA, DNA, and SDS to the hybridization buffer, and treatment with RNase. Wash conditions are typically performed at or below stringency. Exemplary high stringency conditions include carrying out hybridization at a temperature of about 42° C. to about 65° C. for up to about 20 hours in a hybridization medium containing 1M NaCl, 50 mM Tris-HCl, pH 7.4, 10 mM EDTA, 0.1% sodium dodecyl sulfate (SDS), 0.2% ficoll, 0.2% polyvinylpyrrolidone, 0.2% bovine serum albumin, and 50 µg/ml E. coli DNA, followed by washing carried out at between about 42° C. to about 65° C. in a 0.2×SSC buffer.

Variants of suitable hypersensitive response elicitor proteins or polypeptides can also be expressed. Variants may be made by, for example, the deletion, addition, or alteration of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The DNA molecule encoding the hypersensitive response elicitor polypeptide or protein can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in sense orientation and correct reading frame. The vector contains the necessary elements for the transcription and translation of the inserted protein-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," Gene Expression Technology vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., Molecular Cloning: A Laboratory Manual, Cold Springs Laboratory, Cold Springs Harbor, N.Y. (1989), which is hereby incorporated by reference in its entirety.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promotors and accompanying genetic signals may not be recognized in or may not function in a procaryotic system, and, further, procaryotic promotors are not recognized and do not function in eucaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of MRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, Methods in Enzymology, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in E. coli, its bacteriophages, or plasmids, promoters such as the T7 phage promoter, Zac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other E. coli promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon ("ATG") to provide a ribosome binding site. Thus, any SD-ATG combination that can be utilized by host cell ribosomes may be employed. Such combinations include, but are not limited to, the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the DNA molecule coding for a hypersensitive response elicitor protein or polypeptide has been ligated to its appropriate regulatory regions using well known molecular cloning techniques, it can then be introduced into a vector or otherwise introduced directly into a host cell (Sambrook et al., Molecular Cloning: A Laboratory Manual, Second Edition, Cold Spring Harbor Press, N.Y. (1989), which is hereby incorporated by reference in its entirety). The recombinant molecule can be introduced into host cells via transformation, particularly transduction, conjugation, mobilization, or electroporation. Suitable host cells include, but are not limited to, bacteria, virus, yeast, mammalian cells, insect, plant, and the like. Preferably the host cells are either a bacterial cell or a plant cell. The host cells, when grown in an appropriate medium, are capable of expressing the hypersensitive response elicitor protein or polypeptide, which can then be isolated therefrom and, if necessary, purified.

Alternatively, it is desirable for recombinant host cells to secrete the hypersensitive response elicitor protein or polypeptide into growth medium, thereby avoiding the need to lyse cells and remove cellular debris. To enable the host cell to secrete the hypersensitive response elicitor, the host cell can also be transformed with a type III secretion system in accordance with Ham et al., "A Cloned *Erwinia chrysanthemi* Hrp (Type III Protein Secretion) System Functions in *Escherichia coli* to Deliver *Pseudomonas syringae* Avr Signals to Plant Cells and Secrete Avr Proteins in Culture," *Microbiol.* 95:10206-10211 (1998), which is hereby incorporated by reference in its entirety. After growing recombinant host cells which secrete the hypersensitive response elicitor into growth medium, isolation of the hypersensitive response elicitor protein or polypeptide from growth medium can be carried out substantially as described above.

The hypersensitive response elicitor of the present invention is preferably in isolated form (i.e. separated from its host organism) and more preferably produced in purified form (preferably at least about 60%,) by conventional techniques. Typically, the hypersensitive response elicitor of the present invention is produced but not secreted into the growth medium of recombinant host cells. Alternatively, the protein or polypeptide of the present invention is secreted into growth medium. In the case of unsecreted protein, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to heat treatment and the hypersensitive response elicitor is separated by centrifugation. The supernatant fraction containing the hypersensitive response elicitor is subjected to gel filtration in an appropriately sized dextran or polyacrylamide column to separate the fragment. If necessary, the protein fraction may be further purified by ion exchange or HPLC.

A composition suitable for treating plants or plant seeds with a hypersensitive response elicitor polypeptide or protein in an isolated form contains a hypersensitive response elicitor polypeptide or protein in a carrier. Suitable carriers include water, aqueous solutions, slurries, or dry powders. In this embodiment, the composition contains greater than 500 nM hypersensitive response elicitor polypeptide or protein.

Alternatively, application of the hypersensitive response elicitor protein or polypeptide can also be applied in a non-isolated but non-infectious form. When applied in non-isolated but non-infectious form, the hypersensitive response elicitor is applied indirectly to the plant via application of a bacteria which expresses and then secretes or injects the expressed hypersensitive response elicitor protein or polypeptide into plant cells or tissues. Such application can be carried out by applying the bacteria to all or part of a plant or a plant seed under conditions where the polypeptide or protein contacts all or part of the cells of the plant or plant seed. Alternatively, the hypersensitive response elicitor protein or polypeptide can be applied to plants such that seeds recovered from such plants themselves are able to achieve the effects of the present invention.

In the bacterial application mode of the present invention, the bacteria do not cause disease and have been transformed (e.g., recombinantly) with genes encoding a hypersensitive response elicitor polypeptide or protein. For example, *E. coli*, which does not elicit a hypersensitive response in plants, can be transformed with genes encoding a hypersensitive response elicitor polypeptide or protein and then applied to plants. Bacterial species other than *E. coli* can also be used in this embodiment of the present invention.

Alternatively, in the bacterial application mode of the present invention, a naturally occurring virulent bacteria that is capable of expressing and secreting a hypersensitive response elicitor is mutated or altered to be an avirulent pathogen while retaining its ability to express and secrete the hypersensitive response elicitoris. Examples of such naturally occurring virulent bacteria are noted above. In this embodiment, these bacteria are applied to plants or their seeds. For example, virulent *Erwinia amylovora* causes disease in apple. An avirulent *Erwinia amylovora* would not cause the disease in apples, but would retain its ability to express and secrete a hypersensitive response elicitor. Bacterial species other than *Erwinia amylovora* can also be used in this embodiment of the present invention.

The methods of the present invention which involve application of the agricultural chemicals and/or hypersensitive response elicitor polypeptides or proteins can be carried out through a variety of procedures in which all or part of the plant is treated, including leaves, stems, roots, etc. Application techniques may include but not limited to; foliar application, broadcast application, chemigation, high pressures injection, nesting, aerial spray, utilization of chemstations, root drench, and cutting drench. Application may, but need not, involve infiltration of the hypersensitive response elicitor polypeptide or protein into the plant. More than one application of the agricultural chemical and/or hypersensitive response elicitor protein or polypeptide may be desirable to realize maximal benefit over the course of a growing season.

Agricultural chemicals and/or hypersensitive response elicitor polypeptides or proteins can be applied to a plant or plant seed alone or mixed with additional components. Additional components can include one or more additional agricultural chemicals, carriers, adjuvants, buffering agents, coating agents, abrading agents, surfactants, preservatives, and color agents. These materials can be used to facilitate the process of the present invention. In addition, the agricultural chemicals and/or hypersensitive response elicitor polypeptides or proteins can be applied to plant seeds with other conventional seed formulation and treatment materials, including clays and polysaccharides.

When treating plant seeds in accordance with the application embodiment of the present invention, the agricultural chemicals and/or hypersensitive response elicitor polypeptides or proteins can be applied by low or high pressure spraying, seed dusting, seed soaking, and seed coating, or injection. Other suitable application procedures can be envisioned by those skilled in the art provided they are able to effect contact of the hypersensitive response elicitor polypeptide or protein with cells of the plant or plant seed.

Once treated with the agricultural chemical and/or hypersensitive response elicitor of the present invention, the seeds can be planted in natural or artificial soil and cultivated using conventional procedures to produce plants. After plants have been propagated from seeds treated in accordance with the present invention, the plants may also be treated with one or more applications of the agricultural chemicals and/or hypersensitive response elicitor polypeptides or proteins. Such propagated plants may, in turn, be useful in producing seeds or propagules (e.g., cuttings) suitable for carrying out the present invention.

Typically, the manufacturer or distributor's product label for specific agricultural chemicals and/or hypersensitive response elicitor polypeptides or proteins will provide suggested application rates, the crops on which use of the agricultural chemicals and/or hypersensitive response elicitor polypeptides or proteins has been approved, and preferred application techniques if they exist.

The present method, for increasing the efficacy of common agricultural chemicals, can be utilized while treating a wide variety of plants and plant seeds types. Suitable plants include dicots and monocots. More particularly, useful crop plants can include, but are not limited to: canola, alfalfa, rice, wheat, barley, rye, cotton, sunflower, peanut, corn, potato, sweet potato, bean, pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane. Examples of suitable ornamental plants are: *Arabidopsis thaliana, Saintpaulia*, petunia, pelargonium, poinsettia, chrysanthemum, carnation, and zinnia.

In another embodiment of the present invention, one or more agricultural chemicals are applied to a transgenic plants or transgenic seeds encoding a hypersensitive response elicitor protein or polypeptide. This technique involves the use of transgenic plants and transgenic seeds encoding a hypersensitive response elicitor protein or polypeptide, a hypersensitive response elicitor proteins or polypeptides need not be applied to the plant or seed. Instead, transgenic plants transformed with a gene encoding such a hypersensitive response elicitor protein or polypeptide are produced according to procedures well known in the art as described below.

The vector described above can be microinjected directly into plant cells by use of micropipettes to transfer mechanically the recombinant DNA. Crossway, *Mol. Gen. Genetics,* 202:179-85 (1985), which is hereby incorporated by reference in its entirety. The genetic material may also be transferred into the plant cell using polyethylene glycol. Krens, et al., *Nature,* 296:72-74 (1982), which is hereby incorporated by reference in its entirety.

Another approach to transforming plant cells with a gene is particle bombardment (also known as biolistic transformation) of the host cell. This can be accomplished in one of several ways. This technique is disclosed in U.S. Pat. Nos. 4,945,050, 5,036,006, and 5,100,792, all to Sanford et al., which are hereby incorporated by reference in their entirety. Generally, this procedure involves propelling inert or biologically active particles at the cells under conditions effective to penetrate the outer surface of the cell and to be incorporated within the interior thereof When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes, or other fusible lipid-surfaced bodies. Fraley, et al., *Proc. Natl. Acad. Sci. USA,* 79:1859-63 (1982), which is hereby incorporated by reference in its entirety.

The DNA molecule may also be introduced into the plant cells by electroporation. Fromm et al., *Proc. Natl. Acad. Sci. USA,* 82:5824 (1985), which is hereby incorporated by reference in its entirety. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25-28° C.

*Agrobacterium* is a representative genus of the Gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome. J. Schell, *Science,* 237:1176-83 (1987), which is hereby incorporated by reference in its entirety.

After transformation, the transformed plant cells must be regenerated.

Plant regeneration from cultured protoplasts is described in Evans et al., *Handbook of Plant Cell Cultures, Vol.* 1: (MacMillan Publishing Co., New York, 1983); and Vasil I. R. (ed.), *Cell Culture and Somatic Cell Genetics of Plants*, Acad.

Press, Orlando, Vol. I, 1984, and Vol. III (1986), which are hereby incorporated by reference in their entirety.

It is known that practically all plants can be regenerated from cultured cells or tissues, including but not limited to, all major species of sugarcane, sugar beets, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled; then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure. Alternatively, transgenic seeds or propagules (e.g., cuttings) are recovered from the transgenic plants. The seeds can then be planted in the soil and cultivated using conventional procedures to produce transgenic plants. The transgenic plants are propagated from the planted transgenic seeds.

EXAMPLES

Example 1

Application of Messenger® with Roundup UltraMAX® to Improve Control of Various Weeds The objective of this study was to determine if pre, post, or tank-mix application of Messenger (active ingredient harpin$_{Ea}$) affected Roundup UltraMAX's (active ingredient glyphosate, Monsanto, St. Louis, Mo.) ability to control weeds. In this experiment, control of two susceptible and two tolerant dicot weed species, as well as two susceptible and two tolerant monocot weed species was examined. Plots were constructed in the field and uniformilly planted with the respective weed seeds. Plots were maintained in ambient conditions. Messenger and Roundup UltraMAX applications were conducted at 2.25 oz. per acre and 16 oz. per acre, respectively. The various treatment groups were as follows; (1) Messenger application followed three days later by a Roundup UltraMAX application (Mess bf RU), (2) application of Messenger and Roundup UltraMAX at the same time via a tank-mix (MSS+RU), (3) application of Roundup UltraMAX followed one day (24 hours) later by a Messenger application (RU bf MSS), (4) Roundup UltraMAX application alone. Observations regarding the percent weed control of the specific weed species were made at seven and 14 days after treatments (DAT). Results are shown below in Tables 6 through 9.

TABLE 6

Effect of Messenger upon Roundup UltraMAX Efficacy (susceptible dicots)

| Treatment | Common Lambsquarter | | Common Cocklebur | |
|---|---|---|---|---|
| | 7 DAT | 14 DAT | 7 DAT | 14 DAT |
| MSS bf RU | 62 b | 82 b | 82 b | 100 |
| MSS + RU | 73 a | 94 a | 91 a | 100 |
| RU bf MSS | 72 a | 91 a | 92 a | 100 |
| RU | 45 c | 72 c | 72 c | 100 |

Same letters do not significantly differ (P = .05, Student-Newman-Keuls)

TABLE 7

Effect of Messenger upon Roundup UltraMAX Efficacy (tolerant dicots)

| Treatment | Velvetleaf | | Redroot Pigweed | |
|---|---|---|---|---|
| | 7 DAT | 14 DAT | 7 DAT | 14 DAT |
| MSS bf RU | 21 b | 32 b | 54 b | 74 b |
| MSS + RU | 32 a | 44 a | 81 a | 96 a |
| RU bf MSS | 33 a | 46 a | 77 a | 94 a |
| RU | 11 c | 18 c | 35 c | 46 c |

Same letters do not significantly differ (P = .05, Student-Newman-Keuls)

TABLE 8

Effect of Messenger upon Roundup UltraMAX Efficacy (susceptible monocots)

| Treatment | Smooth Crabgrass | | Giant Foxtail | |
|---|---|---|---|---|
| | 7 DAT | 14 DAT | 7 DAT | 14 DAT |
| MSS bf RU | 80 b | 100 | 83 b | 100 |
| MSS + RU | 92 a | 100 | 93 a | 100 |
| RU bf MSS | 91 a | 100 | 92 a | 100 |
| RU | 72 c | 100 | 75 c | 100 |

Same letters do not significantly differ (P = .05, Student-Newman-Keuls)

TABLE 9

Effect of Messenger upon Roundup UltraMAX Efficacy (tolerant monocots)

| Treatment | Yellow Nutsedge | | Shattercane | |
|---|---|---|---|---|
| | 7 DAT | 14 DAT | 7 DAT | 14 DAT |
| MSS bf RU | 5 b | 10 c | 42 b | 70 b |
| MSS + RU | 14 a | 29 a | 75 a | 97 a |
| RU bf MSS | 13 a | 24 d | 72 a | 93 a |
| RU | 2 c | 4 b | 28 c | 54 c |

Same letters do not significantly differ (P = .05, Student-Newman-Keuls)

In each case where 100% control was not achieved, the inclusion of Messenger with Roundup UltraMAX significantly increased Roundup UltraMAX's control of the weed. Though Messenger treatment followed by Roundup UltraMAX treatment showed significantly increased weed control over that of Roundup Ultra Max alone, tank-mixing and application of Roundup UlltraMAX followed by Messenger application showed the greatest control of weeds.

Example 2

Application of Messenger® with Orthene® to Control Insects for Blue Mold in Tobacco Results in Lower Disease Incidence than Orthene Alone Tobacco (*Nicotiana tobacum*), var. K-326, was planted in a small-plot, replicated (3 times) field trial. Application of Messenger (active ingredient harpin$_{Ea}$) Orthene (active ingredient acephate, Valent U.S.A. Corp., Walnut Creek, Calif.), and Messenger+Orthene were made beginning with the transplant water and were followed by 4 foliar sprays at approximately 14-d intervals. Orthene was used in this trial to control aphids, a common vector for blue mold disease (*Peronospora tabacina*) in tobacco.

The trial was not inoculated with insects or disease. Evaluation for blue mold was made approximately one week following the final (4$^{th}$) foliar application of each treatment. Addition of Messenger to the Orthene treatment resulted in lower blue mold infestation than the Messenger alone treatment, while the combination of both products resulted in substantially lower disease incidence than the Orthene alone treatment (Table 10). These results indicate a positive trend for the inclusion of Messenger with Orthene to give a slightly greater disease control than either Messenger or Orthene alone (Table 10).

TABLE 10

Messenger, Orthene, and Messenger + Orthene treatments applied to tobacco as transplant water drenches (TPW) and foliar sprays.

| TREATMENT(S) | APPL. RATE (TPW) | APPL. RATE (FOLIAR SPRAY) | BLUE MOLD DISEASE INCIDENCE (%) |
|---|---|---|---|
| Messenger | 30 ppm | 30 ppm | 8.2 |
| Orthene | 12 oz/A | 12 oz/A | 27.8 |
| Messenger + Orthene | 30 ppm + 12 oz/A | 30 ppm + 12 oz/A | 7.0 |

Messenger vs. Messenger+Orthene: 15% decrease in blue mold disease incidence.

Orthene vs. Messenger+Orthene: 75% decrease in blue mold disease incidence.

Example 3

Application of Messenger® with Temik® to Control Nematodes in Cotton Enhances Performance of Temik Cotton, (*Gossypium hirsutum*), var. PM 1218, was planted to a small-plot, replicated (6 times) field trial. Plot size was 6-8 rows×50 feet with the center 4 rows treated and center 2 rows harvested. Ten-foot buffers were established between blocks. Temik (active ingredient aldricarb, Aventis CropScience, Research Triangle, N.C.) was applied in-furrow (at 5 lbs/A) at planting. Messenger (active ingredient harpin$_{Ea}$) foliar applications (at 2.23 oz/A) were made at various timing regimes on both Temik-treated and non-Temik treated cotton. Yield data in response to these treatments is shown in Table 11.

TABLE 11

Messenger, Temik, and Messenger + Temik Treatments Effect on Cotton Seed Yield.

| TREATMENT | SEED COTTOT SEED YIELD (LBS/A) | INCREASE OVER UNTREATED (%) |
|---|---|---|
| Messenger | 2,203[1] | 8.9 |
| Messenger + Temik | 2,388[1] | 18.0 |
| Temik | 2,221 | 9.8 |
| Untreated | 2,023 | — |

[1]Seed cotton yield figures are averages from four treatment-timing combinations of Messenger and Messenger + Temik, respectively.

Results from this field trial indicated that both the individual Messenger and Temik treatments boosted seed cotton yield about 10% above the untreated. However, the Messenger+Temik treatment gave an 18% yield above the untreated suggesting that addition of Messenger to the Temik treatment enhanced Temik's ability to perform its intended function.

Example 4

Application of Messenger® with Equation Pro® to Control Late Blight in Tomatoes Enhances Performance of Equation Pro Tomato seedlings were planted into greenhouse pots, 3 plants per pot replicated 4 pots per treatment. One week prior to artificial inoculation with *Phytopthora infestans* (Late blight), one set of plants received a single foliar spray of Messenger (active ingredient harpin$_{Ea}$) at approx. 20 ppm active ingredient (a.i.) followed by a second foliar spray approximately one week after inoculation. A second set of replicate pots received Messenger+Equation Pro (active ingredients famoxadone+cymoxanil, DuPont Crop Protection, Wilmington, Del.) while a third set of replicates received only the Equation Pro treatment. An untreated control treatment was included in the test. After the disease had spread to fully infect the untreated plants, treated plants were rated for disease symptoms; severity and index were both calculated for each treatment. Results are presented in Table 12.

TABLE 12

Messenger, Messenger + Equation Pro, and Equation Pro Treatments Effect on Late Blight in Tomato.

| TREATMENT | DISEASE INDEX | SEVERITY (%) | EFFICACY (%) |
|---|---|---|---|
| Messenger | 0.89[1] | 17.9 | 71.0 |
| Messenger + Equation Pro | 0.30[1] | 6.0 | 90.2 |
| Equation Pro | 0.59 | 11.8 | 80.8 |
| Untreated | 3.07 | 61.4 | — |

[1]Mean values of four replicate pots, three plants in each.

Results from this greenhouse trial indicated that both the individual Messenger and Equation Pro treatments provided substantial resistance to Late blight in tomato. However, the Messenger+Equation Pro treatment resulted in an even greater degree of disease control than either treatment alone, suggesting that the addition of Messenger to the Equation Pro treatment enhances Equation Pro's ability to perform its intended function.

Example 5

Inclusion of Messenger® in Aliette® Treatment Program Increases Control of *Phytophthora cinnamomi* Root Rot in Avocado Five month old avocado seedlings (Topo Topa) were inoculated with *Phytophthora cinnamomi*. Treatment groups included; (1) Aliette (active ingredient fosetyl-aluminum ISO, Aventis CropScience, Research Triangle Park, N.C.) pre-treatment, applied seven days prior to inoculation, (2) Messenger (active ingredient harpin$_{Ea}$) treatments seven days prior to inoculation, 14 days post-inoculation and every 21 days there after, (3) the combination of treatments 1 and 2 described above, (4) inoculated untreated control, and (5) uninoculated untreated control. Each treatment group was replicated six times. Observations were recorded with respect to the percent of necrotic roots present in the total root mass. Avocado roots show a distinct blackening when infected with *P. cinnamomi*, whereas non-infected roots are brown-white in color. Table 13 summarizes the study details and resulting data.

TABLE 13

Messenger, Messenger + Aliette, and Aliette Treatments Effect on Root Rot in Avocado.

| Treatment | Application Technique | % Diseased Roots |
| --- | --- | --- |
| Aliette | pre-treatment | 60 bc |
| Messenger | foliar every 21 days | 38.3 c |
| Aliette + Messenger | pre-treat + foliar 21 d | 27.5 cd |
| UTC | none | 96.5 a |
| UTC (no inoculation) | none | 6.3 d |

Same letters do not significantly differ.

Although the invention has been described in detail for the purpose of illustration, it is understood that such details are solely for that purpose, and variations can be made therein by those skilled in the art without departing from the spirit of the scope of the invention which is defined by the following claims.

```

What is claimed is:

1. A method of treating at least one plant or plant seed with at least one insecticide, fungicide, or herbicide where a local population of pests has resistance to the at least one insecticide, fungicide, or herbicide, said method comprising:

selecting the at least one plant or plant seed to be treated by the at least one insecticide, fungicide, or herbicide under conditions effective for the at least one insecticide, fungicide, or herbicide to perform its intended function, wherein the selected at least one plant or plant seed is planted where the local population of pests has resistance to the at least one insecticide, fungicide, or herbicide and applying the at least one insecticide, fungicide, or herbicide and at least one hypersensitive response elicitor protein or polypeptide to said selected at least one plant or plant seed under conditions effective to treat the at least one plant or plant seed with the at least one insecticide, fungicide, or herbicide, wherein said at least one hypersensitive response elicitor is heat stable, glycine rich, and contains substantially no cysteine.

2. The method according to claim 1, wherein said selected plant is treated during said applying.

3. The method according to claim 1, wherein said selected plant seed is treated during said applying, said method further comprising:

planting said treated, selected plant seed in natural or artificial soil and propagating a plant from said treated, selected plant seed planted in said natural or artificial soil.

4. The method according to claim 1, wherein said selected plants or plant seeds are selected from the group consisting of canola, alfalfa, rice, wheat, barley, rye, cotton, sunflower, peanut, corn, potato, sweet potato, bean, pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, avocado, sugarcane, Saintpaulia, petunia, pelargonium, poinsettia, chrysanthemum, carnation, and zinnia.

5. The method according to claim 1, wherein said applying the at least one insecticide, fungicide, or herbicide is conducted simultaneously or independently of said applying the at least one hypersensitive response elicitor protein or polypeptide.

6. The method according to claim 1, wherein the at least one insecticide is applied, said insecticide containing an active ingredient selected from the group consisting of carbamates, organochlorines, nicotinoids, phosphoramidothioates, organophosphates, and pyrethroids.

7. The method according to claim 1, wherein the at least one fungicide is applied, said fungicide containing an active ingredient selected from the group consisting of aliphatic nitrogens, benzimidazoles, dicarboximides, dithiocarbamates, imidazoles, strobins, anilides, aromatics, sulfur derivatives, and copper derivatives.

8. The method according to claim 1, wherein the at least one herbicide is applied, said herbicide is selected from the group consisting of acetyl-CoA carboxylase inhibitors (ACCase), actolactate synthase inhibitors (ALS), microtubule assembly inhibitors (MT), growth regulators (GR), photosynthesis II, binding site A inhibitors (PSII(A)), photosynthesis II, binding site B inhibitors (PSII(B)), photosynthesis II, binding site C inhibitors (PSII(C)), shoot inhibitors (SHT), enolpyruvyl-shikimate-phosphate synthase inhibitors (EPSP), glutamine synthase inhibitors (GS), phytoene desaturase synthase inhibitors (PDS), diterpene inhibitors (DITERP), protoporphyrinogen oxidase inhibitors (PPO), shoot and root inhibitors (SHT/RT), photosystem 1 electron diverters (ED), hydroxyphenlypyruvate dioxygenase synthesis inhibitors (HPPD), and combinations thereof.

9. The method according to claim 1, wherein the at least one hypersensitive response elicitor or polypeptide is derived from a species of pathogens selected from the group consisting of *Erwinia, Pseudomonas*, and *Xanthomonas*.

10. The method according to claim 9, wherein the at least one hypersensitive response elicitor protein or polypeptide is derived from an *Erwinia* species selected from the group consisting of *Erwinia amylovora, Erwinia carotovora, Erwinia chrysanthemi,* and *Erwinia stewartii.*

11. The method according to claim 9, wherein the at least one hypersensitive response elicitor protein or polypeptide is derived from a *Pseudomonas* species selected from the group consisting of *Pseudomonas syringae* and *Pseudomonas solanacearum.*

12. The method according to claim 9, wherein the at least one hypersensitive response elicitor or polypeptide is derived from *Xanthomonas campestris.*

13. The method according to claim 1, wherein the at least one insecticide is applied, said insecticide comprising nicotinoid.

14. The method according to claim 1, wherein the at least one fungicide is applied, said fungicide comprising strobin.

15. The method according to claim 1, wherein the at least one herbicide is applied, said herbicide comprising glyphosate.

16. The method according to claim 1, wherein the at least one herbicide and the at least one fungicide are applied, said herbicide comprising glyphosate and said fungicide comprising strobin.

17. The method according to claim 1, wherein the at least one herbicide and the at least one insecticide are applied, said herbicide comprising glyphosate and said insecticide comprising nicotinoid.

18. The method according to claim 1, wherein the at least one herbicide is applied, said herbicide comprising glyphosate and Dicamba.

19. The method according to claim 1, wherein the at least one herbicide and the at least one fungicide are applied, said herbicide comprising glyphosate, and Dicamba, and said fungicide comprising strobin.

20. The method according to claim 1, wherein the at least one herbicide and the at least one insecticide are applied, said herbicide comprising glyphosate, and Dicamba, and said insecticide comprising nicotinoid.

21. The method according to claim 8, wherein the at least one herbicide is applied, said herbicide comprising a enolpyruvyl-shikimate-phosphate synthase inhibitor (EPSP) glyphosate.

22. The method according to claim 6, wherein the at least one insecticide is applied, said insecticide comprising a pyrethroid.

23. The method according to claim 7, wherein the at least one fungicide is applied, said fungicide comprising a benzimidazole.

24. A method of treating at least one transgenic plant or transgenic seed with at least one insecticide, fungicide, or herbicide where a local population of pests has resistance to the at least one insecticide, fungicide, or herbicide, said method comprising:

selecting the at least one transgenic plant or transgenic seed, transformed with at least one nucleic acid molecule which encodes at least one hypersensitive response elicitor protein or polypeptide, to be treated by the at least one insecticide, fungicide, or herbicide under conditions effective for the at least one insecticide, fungicide, or herbicide to treat at least one pest, wherein the selected at least one transgenic plant or transgenic seed is planted where the local population of pests has resistance to the at least one insecticide, fungicide, or herbicide and applying the at least one insecticide, fungicide, or herbicide to said selected transgenic plant or transgenic seed under conditions effective to treat the at least one transgenic plant or transgenic seed with the at least one insecticide, fungicide, or herbicide and for the at least one insecticide, fungicide, or herbicide to perform its intended functions, wherein said at least one hypersensitive response elicitor is heat stable, glycine rich, and contains substantially no cysteine.

\* \* \* \* \*

                       SEQUENCE LISTING

<160> NUMBER OF SEQ ID NOS: 14

<210> SEQ ID NO 1
<211> LENGTH: 338
<212> TYPE: PRT
<213> ORGANISM: Erwinia chrysanthemi

<400> SEQUENCE: 1

Met Gln Ile Thr Ile Lys Ala His Ile Gly Gly Asp Leu Gly Val Ser
1               5                   10                  15

Gly Leu Gly Ala Gln Gly Leu Lys Gly Leu Asn Ser Ala Ala Ser Ser
            20                  25                  30

Leu Gly Ser Ser Val Asp Lys Leu Ser Ser Thr Ile Asp Lys Leu Thr
        35                  40                  45

Ser Ala Leu Thr Ser Met Met Phe Gly Gly Ala Leu Ala Gln Gly Leu
    50                  55                  60

Gly Ala Ser Ser Lys Gly Leu Gly Met Ser Asn Gln Leu Gly Gln Ser
65                  70                  75                  80

Phe Gly Asn Gly Ala Gln Gly Ala Ser Asn Leu Leu Ser Val Pro Lys
                85                  90                  95

Ser Gly Gly Asp Ala Leu Ser Lys Met Phe Asp Lys Ala Leu Asp Asp
            100                 105                 110

Leu Leu Gly His Asp Thr Val Thr Lys Leu Thr Asn Gln Ser Asn Gln
        115                 120                 125

Leu Ala Asn Ser Met Leu Asn Ala Ser Gln Met Thr Gln Gly Asn Met
    130                 135                 140

Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
            180                 185                 190

Gly Asn Ala Ile Gly Met Gly Val Gly Gln Asn Ala Ala Leu Ser Ala
        195                 200                 205

Leu Ser Asn Val Ser Thr His Val Asp Gly Asn Asn Arg His Phe Val
```

```
              210                 215                 220
Asp Lys Glu Asp Arg Gly Met Ala Lys Glu Ile Gly Gln Phe Met Asp
225                 230                 235                 240

Gln Tyr Pro Glu Ile Phe Gly Lys Pro Glu Tyr Gln Lys Asp Gly Trp
                245                 250                 255

Ser Ser Pro Lys Thr Asp Asp Lys Ser Trp Ala Lys Ala Leu Ser Lys
                260                 265                 270

Pro Asp Asp Gly Met Thr Gly Ala Ser Met Asp Lys Phe Arg Gln
                275                 280                 285

Ala Met Gly Met Ile Lys Ser Ala Val Ala Gly Asp Thr Gly Asn Thr
290                 295                 300

Asn Leu Asn Leu Arg Gly Ala Gly Gly Ala Ser Leu Gly Ile Asp Ala
305                 310                 315                 320

Ala Val Val Gly Asp Lys Ile Ala Asn Met Ser Leu Gly Lys Leu Ala
                325                 330                 335

Asn Ala

<210> SEQ ID NO 2
<211> LENGTH: 2141
<212> TYPE: DNA
<213> ORGANISM: Erwinia chrysanthemi

<400> SEQUENCE: 2
cgattttacc cgggtgaacg tgctatgacc gacagcatca cggtattcga caccgttacg      60
gcgtttatgg ccgcgatgaa ccggcatcag gcggcgcgct ggtcgccgca atccggcgtc     120
gatctggtat ttcagtttgg ggacaccggg cgtgaactca tgatgcagat tcagccgggg     180
cagcaatatc ccggcatgtt gcgcacgctg ctcgctcgtc gttatcagca ggcggcagag     240
tgcgatggct gccatctgtg cctgaacggc agcgatgtat tgatcctctg gtggccgctg     300
ccgtcggatc ccggcagtta ccgcaggtg atcgaacgtt tgtttgaact ggcgggaatg     360
acgttgccgt cgctatccat agcaccgacg gcgcgtccgc agacagggaa cggacgcgcc     420
cgatcattaa gataaaggcg ctttttttta ttgcaaaacg gtaacggtga ggaaccgttt     480
caccgtcggc gtcactcagt aacaagtatc catcatgatg cctacatcgg gatcggcgtg     540
ggcatccgtt gcagatactt ttgcgaacac ctgacatgaa tgaggaaacg aaattatgca     600
aattacgatc aaagcgcaca tcggcggtga tttgggcgtc tccggtctgg ggctgggtgc     660
tcagggactg aaaggactga attccgcggc ttcatcgctg ggttccagcg tggataaact     720
gagcagcacc atcgataagt tgacctccgc gctgacttcg atgatgtttg cggcgcgct     780
ggcgcagggg ctgggcgcca gctcgaaggg gctggggatg agcaatcaac tgggccagtc     840
tttcggcaat ggcgcgcagg gtgcgagcaa cctgctatcc gtaccgaaat ccggcggcga     900
tgcgttgtca aaatgtttg ataaagcgct ggacgatctg ctgggtcatg acaccgtgac     960
caagctgact aaccagagca accaactggc taattcaatg ctgaacgcca gccagatgac    1020
ccagggtaat atgaatgcgt tcggcagcgg tgtgaacaac gcactgtcgt ccattctcgg    1080
caacggtctc ggccagtcga tgagtggctt ctctcagcct tctctggggg caggcggctt    1140
gcagggcctg agcggcgcgg gtgcattcaa ccagttgggt aatgccatcg gcatgggcgt    1200
ggggcagaat gctgcgctga gtgcgttgag taacgtcagc acccacgtag acggtaacaa    1260
ccgccacttt gtagataaag aagatcgcgg catggcgaaa gagatcggcc agtttatgga    1320
tcagtatccg gaaatattcg gtaaaccgga ataccagaaa gatggctgga gttcgccgaa    1380
gacggacgac aaatcctggg ctaaagcgct gagtaaaccg gatgatgacg gtatgaccgg    1440
```

```
cgccagcatg gacaaattcc gtcaggcgat gggtatgatc aaaagcgcgg tggcgggtga      1500
taccggcaat accaacctga acctgcgtgg cgcgggcggt gcatcgctgg gtatcgatgc      1560
ggctgtcgtc ggcgataaaa tagccaacat gtcgctgggt aagctggcca acgcctgata      1620
atctgtgctg gcctgataaa gcggaaacga aaaagagac ggggaagcct gtctctttttc     1680 ttattatgcg gttatgcgg ttacctggac cggttaatca tcgtcatcga tctggtacaa      1740
acgcacattt tcccgttcat tcgcgtcgtt acgcgccaca atcgcgatgg catcttcctc     1800
gtcgctcaga ttgcgcggct gatggggaac gccgggtgga atatagagaa actcgccggc     1860
cagatggaga cacgtctgcg ataaatctgt gccgtaacgt gtttctatcc gcccctttag     1920
cagatagatt gcggtttcgt aatcaacatg gtaatgcggt tccgcctgtg cgccggccgg     1980
gatcaccaca atattcatag aaagctgtct tgcacctacc gtatcgcggg agataccgac     2040
aaaatagggc agttttttgcg tggtatccgt ggggtgttcc ggcctgacaa tcttgagttg    2100
gttcgtcatc atctttctcc atctgggcga cctgatcggt t                         2141

<210> SEQ ID NO 3
<211> LENGTH: 403
<212> TYPE: PRT
<213> ORGANISM: Erwinia amylovora - harpinEa

<400> SEQUENCE: 3

Met Ser Leu Asn Thr Ser Gly Leu Gly Ala Ser Thr Met Gln Ile Ser
1               5                   10                  15

Ile Gly Gly Ala Gly Gly Asn Asn Gly Leu Leu Gly Thr Ser Arg Gln
            20                  25                  30

Asn Ala Gly Leu Gly Gly Asn Ser Ala Leu Gly Leu Gly Gly Gly Asn
        35                  40                  45

Gln Asn Asp Thr Val Asn Gln Leu Ala Gly Leu Leu Thr Gly Met Met
    50                  55                  60

Met Met Met Ser Met Met Gly Gly Gly Gly Leu Met Gly Gly Gly Leu
65                  70                  75                  80

Gly Gly Gly Leu Gly Asn Gly Leu Gly Gly Ser Gly Gly Leu Gly Glu
                85                  90                  95

Gly Leu Ser Asn Ala Leu Asn Asp Met Leu Gly Gly Ser Leu Asn Thr
            100                 105                 110

Leu Gly Ser Lys Gly Gly Asn Asn Thr Thr Ser Thr Thr Asn Ser Pro
        115                 120                 125

Leu Asp Gln Ala Leu Gly Ile Asn Ser Thr Ser Gln Asn Asp Asp Ser
    130                 135                 140

Thr Ser Gly Thr Asp Ser Thr Ser Asp Ser Ser Asp Pro Met Gln Gln
145                 150                 155                 160

Leu Leu Lys Met Phe Ser Glu Ile Met Gln Ser Leu Phe Gly Asp Gly
                165                 170                 175

Gln Asp Gly Thr Gln Gly Ser Ser Ser Gly Gly Lys Gln Pro Thr Glu
            180                 185                 190

Gly Glu Gln Asn Ala Tyr Lys Lys Gly Val Thr Asp Ala Leu Ser Gly
        195                 200                 205

Leu Met Gly Asn Gly Leu Ser Gln Leu Leu Gly Asn Gly Gly Leu Gly
    210                 215                 220

Gly Gly Gln Gly Gly Asn Ala Gly Thr Gly Leu Asp Gly Ser Ser Leu
225                 230                 235                 240

Gly Gly Lys Gly Leu Gln Asn Leu Ser Gly Pro Val Asp Tyr Gln Gln
                245                 250                 255
```

Leu Gly Asn Ala Val Gly Thr Gly Ile Gly Met Lys Ala Gly Ile Gln
        260                 265                 270

Ala Leu Asn Asp Ile Gly Thr His Arg His Ser Ser Thr Arg Ser Phe
        275                 280                 285

Val Asn Lys Gly Asp Arg Ala Met Ala Lys Glu Ile Gly Gln Phe Met
        290                 295                 300

Asp Gln Tyr Pro Glu Val Phe Gly Lys Pro Gln Tyr Gln Lys Gly Pro
305                 310                 315                 320

Gly Gln Glu Val Lys Thr Asp Asp Lys Ser Trp Ala Lys Ala Leu Ser
                325                 330                 335

Lys Pro Asp Asp Gly Met Thr Pro Ala Ser Met Glu Gln Phe Asn
                340                 345                 350

Lys Ala Lys Gly Met Ile Lys Arg Pro Met Ala Gly Asp Thr Gly Asn
                355                 360                 365

Gly Asn Leu Gln Ala Arg Gly Ala Gly Gly Ser Ser Leu Gly Ile Asp
        370                 375                 380

Ala Met Met Ala Gly Asp Ala Ile Asn Asn Met Ala Leu Gly Lys Leu
385                 390                 395                 400

Gly Ala Ala

<210> SEQ ID NO 4
<211> LENGTH: 1288
<212> TYPE: DNA
<213> ORGANISM: Erwinia amylovora - harpinEa

<400> SEQUENCE: 4
aagcttcggc atggcacgtt tgaccgttgg gtcggcaggg tacgttttgaa ttattcataa        60
gaggaatacg ttatgagtct gaatacaagt gggctgggag cgtcaacgat gcaaatttct       120
atcggcggtg cgggcggaaa taacgggttg ctgggtacca gtcgccagaa tgctgggttg       180
ggtggcaatt ctgcactggg gctgggcggc ggtaatcaaa atgataccgt caatcagctg       240
gctggcttac tcaccggcat gatgatgat atgagcatga tgggcggtgg tgggctgatg       300
ggcggtggct taggcggtgg cttaggtaat ggcttgggtg gctcaggtgg cctgggcgaa       360
ggactgtcga acgcgctgaa cgatatgtta ggcggttcgc tgaacacgct gggctcgaaa       420
ggcggcaaca ataccacttc aacaacaaat tcccgctgg accaggcgct gggtattaac       480
tcaacgtccc aaaacgacga ttccacctcc ggcacagatt ccacctcaga ctccagcgac       540
ccgatgcagc agctgctgaa gatgttcagc gagataatgc aaagcctgtt tggtgatggg       600
caagatggca cccagggcag ttcctctggg ggcaagcagc cgaccgaagg cgagcagaac       660
gcctataaaa aaggagtcac tgatgcgctg tcgggcctga tgggtaatgg tctgagccag       720
ctccttggca acggggact gggaggtggt cagggcggta atgctggcac gggtcttgac       780
ggttcgtcgc tggcggcaa agggctgcaa aacctgagcg gccggtgga ctaccagcag       840
ttaggtaacg ccgtgggtac cggtatcggt atgaaagcgg gcattcaggc gctgaatgat       900
atcggtacgc acaggcacag ttcaacccgt tctttcgtca ataaaggcga tcgggcgatg       960
gcgaaggaaa tcggtcagtt catggaccag tatcctgagg tgtttggcaa gccgcagtac      1020
cagaaaggcc cgggtcagga ggtgaaaacc gatgacaaat catgggcaaa agcactgagc      1080
aagccagatg acgacggaat gacaccagcc agtatggagc agttcaacaa agccaagggc      1140
atgatcaaaa ggcccatggc gggtgatacc ggcaacggca acctgcaggc acgcggtgcc      1200
ggtggttctt cgctgggtat tgatgccatg atggccggtg atgccattaa caatatggca      1260
cttggcaagc tgggcgcggc ttaagctt                                                                    1288

<210> SEQ ID NO 5
<211> LENGTH: 447
<212> TYPE: PRT
<213> ORGANISM: Erwinia amylovora

<400> SEQUENCE: 5

```
Met Ser Ile

```
                370                 375                 380
Val Arg Thr Asn Gly Gly Gln Gln Gly Asn Trp Asp Leu Asn Leu Ser
385                 390                 395                 400

His Ile Ser Ala Glu Asp Gly Lys Phe Ser Phe Val Lys Ser Asp Ser
                405                 410                 415

Glu Gly Leu Asn Val Asn Thr Ser Asp Ile Ser Leu Gly Asp Val Glu
                420                 425                 430

Asn His Tyr Lys Val Pro Met Ser Ala Asn Leu Lys Val Ala Glu
                435                 440                 445

<210> SEQ ID NO 6
<211> LENGTH: 1344
<212> TYPE: DNA
<213> ORGANISM: Erwinia amylovora

<400> SEQUENCE:

|  |  |  |  | 20 |  |  |  | 25 |  |  |  | 30 |  |  |
|---|---|---|---|---|---|---|---|---|---|---|---|---|---|---|

Ser Lys Ala Leu Gln Glu Val Val Lys Leu Ala Glu Glu Leu Met
        35                40                45

Arg Asn Gly Gln Leu Asp Asp Ser Ser Pro Leu Gly Lys Leu Leu Ala
  50                  55                60

Lys Ser Met Ala Ala Asp Gly Lys Ala Gly Gly Ile Glu Asp Val
65                70                75              80

Ile Ala Ala Leu Asp Lys Leu Ile His Glu Lys Leu Gly Asp Asn Phe
                85                90              95

Gly Ala Ser Ala Asp Ser Ala Ser Gly Thr Gly Gln Gln Asp Leu Met
          100                105              110

Thr Gln Val Leu Asn Gly Leu Ala Lys Ser Met Leu Asp Asp Leu Leu
        115                120              125

Thr Lys Gln Asp Gly Gly Thr Ser Phe Ser Glu Asp Met Pro Met
130               135                140

Leu Asn Lys Ile Ala Gln Phe Met Asp Asp Asn Pro Ala Gln Phe Pro
145                150                155              160

Lys Pro Asp Ser Gly Ser Trp Val Asn Glu Leu Lys Glu Asp Asn Phe
                165              170              175

Leu Asp Gly Asp Glu Thr Ala Ala Phe Arg Ser Ala Leu Asp Ile Ile
          180                185              190

Gly Gln Gln Leu Gly Asn Gln Gln Ser Asp Ala Gly Ser Leu Ala Gly
        195              200              205

Thr Gly Gly Leu Gly Thr Pro Ser Ser Phe Ser Asn Asn Ser Ser
        210                215              220

Val Met Gly Asp Pro Leu Ile Asp Ala Asn Thr Gly Pro Gly Asp Ser
225                230                235              240

Gly Asn Thr Arg Gly Glu Ala Gly Gln Leu Ile Gly Glu Leu Ile Asp
                245              250              255

Arg Gly Leu Gln Ser Val Leu Ala Gly Gly Gly Leu Gly Thr Pro Val
          260                265              270

Asn Thr Pro Gln Thr Gly Thr Ser Ala Asn Gly Gly Gln Ser Ala Gln
        275                280              285

Asp Leu Asp Gln Leu Leu Gly Gly Leu Leu Lys Gly Leu Glu Ala
        290                295              300

Thr Leu Lys Asp Ala Gly Gln Thr Gly Thr Asp Val Gln Ser Ser Ala
305                310                315              320

Ala Gln Ile Ala Thr Leu Leu Val Ser Thr Leu Leu Gln Gly Thr Arg
                325              330              335

Asn Gln Ala Ala Ala
        340

<210> SEQ ID NO 8
<211> LENGTH: 1026
<212> TYPE: DNA
<213> ORGANISM: Pseudomonas syringae

<400> SEQUENCE: 8

```
atgcagagtc tcagtcttaa cagcagctcg ctgcaaaccc cggcaatggc ccttgtcctg      60
gtacgtcctg aagccgagac gactggcagt acgtcgagca aggcgcttca ggaagttgtc     120
gtgaagctgg ccgaggaact gatgcgcaat ggtcaactcg acgacagctc gccattggga     180
aaactgttgg ccaagtcgat ggccgcagat ggcaaggcgg gcggcggtat tgaggatgtc     240
atcgctgcgc tggacaagct gatccatgaa aagctcggtg acaacttcgg cgcgtctgcg     300
```

```
gacagcgcct cgggtaccgg acagcaggac ctgatgactc aggtgctcaa tggcctggcc    360
aagtcgatgc tcgatgatct tctgaccaag caggatggcg ggacaagctt ctccgaagac    420
gatatgccga tgctgaacaa gatcgcgcag ttcatggatg acaatcccgc acagtttccc    480
aagccggact cgggctcctg ggtgaacgaa ctcaaggaag acaacttcct tgatggcgac    540
gaaacggctg cgttccgttc ggcactcgac atcattggcc agcaactggg taatcagcag    600
agtgacgctg gcagtctggc agggacgggt ggaggtctgg cactccgag cagttttttcc    660
aacaactcgt ccgtgatggg tgatccgctg atcgacgcca ataccggtcc cggtgacagc    720
ggcaataccc gtggtgaagc ggggcaactg atcggcgagc ttatcgaccg tggcctgcaa    780
tcggtattgg ccggtggtgg actgggcaca cccgtaaaca ccccgcagac cggtacgtcg    840
gcgaatggcg acagtccgc tcaggatctt gatcagttgc tgggcggctt gctgctcaag    900
ggcctggagg caacgctcaa ggatgccggg caaacaggca ccgacgtgca gtcgagcgct    960
gcgcaaatcg ccaccttgct ggtcagtacg ctgctgcaag gcacccgcaa tcaggctgca   1020
gcctga                                                               1026
```

<210> SEQ ID NO 9
<211> LENGTH: 424
<212> TYPE: PRT
<213> ORGANISM: Pseudomonas syringae

<400> SEQUENCE: 9

```
Met Ser Ile Gly Ile Thr Pro Arg Pro Gln Thr Thr Thr Pro Leu
1               5                   10                  15

Asp Phe Ser Ala Leu Ser Gly Lys Ser Pro Gln Pro Asn Thr Phe Gly
            20                  25                  30

Glu Gln Asn Thr Gln Gln Ala Ile Asp Pro Ser Ala Leu Leu Phe Gly
        35                  40                  45

Ser Asp Thr Gln Lys Asp Val Asn Phe Gly Thr Pro Asp Ser Thr Val
    50                  55                  60

Gln Asn Pro Gln Asp Ala Ser Lys Pro Asn Asp Ser Gln Ser Asn Ile
65                  70                  75                  80

Ala Lys Leu Ile Ser Ala Leu Ile Met Ser Leu Leu Gln Met Leu Thr
                85                  90                  95

Asn Ser Asn Lys Lys Gln Asp Thr Asn Gln Glu Gln Pro Asp Ser Gln
            100                 105                 110

Ala Pro Phe Gln Asn Asn Gly Gly Leu Gly Thr Pro Ser Ala Asp Ser
        115                 120                 125

Gly Gly Gly Gly Thr Pro Asp Ala Thr Gly Gly Gly Gly Asp Thr
    130                 135                 140

Pro Ser Ala Thr Gly Gly Gly Gly Asp Thr Pro Thr Ala Thr Gly
145                 150                 155                 160

Gly Gly Gly Ser Gly Gly Gly Thr Pro Thr Ala Thr Gly Gly
                165                 170                 175

Ser Gly Gly Thr Pro Thr Ala Thr Gly Gly Glu Gly Gly Val Thr
            180                 185                 190

Pro Gln Ile Thr Pro Gln Leu Ala Asn Pro Asn Arg Thr Ser Gly Thr
        195                 200                 205

Gly Ser Val Ser Asp Thr Ala Gly Ser Thr Glu Gln Ala Gly Lys Ile
    210                 215                 220

Asn Val Val Lys Asp Thr Ile Lys Val Gly Ala Gly Glu Val Phe Asp
225                 230                 235                 240

Gly His Gly Ala Thr Phe Thr Ala Asp Lys Ser Met Gly Asn Gly Asp
```

```
                    245                 250                 255
Gln Gly Glu Asn Gln Lys Pro Met Phe Glu Leu Ala Glu Gly Ala Thr
            260                 265                 270

Leu Lys Asn Val Asn Leu Gly Glu Asn Glu Val Asp Gly Ile His Val
        275                 280                 285

Lys Ala Lys Asn Ala Gln Glu Val Thr Ile Asp Asn Val His Ala Gln
        290                 295                 300

Asn Val Gly Glu Asp Leu Ile Thr Val Lys Gly Glu Gly Gly Ala Ala
305                 310                 315                 320

Val Thr Asn Leu Asn Ile Lys Asn Ser Ser Ala Lys Gly Ala Asp Asp
                325                 330                 335

Lys Val Val Gln Leu Asn Ala Asn Thr His Leu Lys Ile Asp Asn Phe
            340                 345                 350

Lys Ala Asp Asp Phe Gly Thr Met Val Arg Thr Asn Gly Gly Lys Gln
        355                 360                 365

Phe Asp Asp Met Ser Ile Glu Leu Asn Gly Ile Glu Ala Asn His Gly
        370                 375                 380

Lys Phe Ala Leu Val Lys Ser Asp Ser Asp Leu Lys Leu Ala Thr
385                 390                 395                 400

Gly Asn Ile Ala Met Thr Asp Val Lys His Ala Tyr Asp Lys Thr Gln
                405                 410                 415

Ala Ser Thr Gln His Thr Glu Leu
            420

<210> SEQ ID NO 10
<211> LENGTH: 1729
<212> TYPE: DNA
<213> ORGANISM: Pseudomonas syringae

<400> SEQUENCE: 10
tccacttcgc tgattttgaa attggcagat tcatagaaac gttcaggtgt ggaaatcagg      60
ctgagtgcgc agatttcgtt gataagggtg tggtactggt cattgttggt catttcaagg     120
cctctgagtg cggtgcggag caataccagt cttcctgctg gcgtgtgcac actgagtcgc     180
aggcataggc atttcagttc cttgcgttgg ttgggcatat aaaaaaagga acttttaaaa     240
acagtgcaat gagatgccgg caaaacggga accggtcgct gcgctttgcc actcacttcg     300
agcaagctca accccaaaca tccacatccc tatcgaacgg acagcgatac ggccacttgc     360
tctggtaaac cctggagctg gcgtcggtcc aattgcccac ttagcgaggt aacgcagcat     420
gagcatcggc atcacacccc ggccgcaaca gaccaccacg ccactcgatt tttcggcgct     480
aagcggcaag agtcctcaac caaacacgtt cggcgagcag aacactcagc aagcgatcga     540
cccgagtgca ctgttgttcg gcagcgacac acagaaagac gtcaacttcg gcacgcccga     600
cagcaccgtc cagaatccgc aggacgccag caagcccaac gacagccagt ccaacatcgc     660
taaattgatc agtgcattga tcatgtcgtt gctgcagatg ctcaccaact ccaataaaaa     720
gcaggacacc aatcaggaac agcctgatag ccaggctcct ttccagaaca acggcgggct     780
cggtacaccg tcggccgata gcgggggcgg cggtacaccg gatgcgacag gtggcggcgg     840
cggtgatacg ccaagcgcaa caggcggtgg cggcggtgat actccgaccg caacaggcgg     900
tggcggcagc ggtggcggcg gcacacccac tgcaacaggg gcggcagcg gtggcacacc     960 cactgcaaca gcggtggcg agggtggcgt aacaccgcaa atcactccgc agttggccaa    1020
ccctaaccgt acctcaggta ctggctcggt gtcggacacc gcaggttcta ccgagcaagc    1080
cggcaagatc aatgtggtga agacaccat caaggtcggc gctggcgaag tctttgacgg    1140
```

```
ccacggcgca accttcactg ccgacaaatc tatgggtaac ggagaccagg gcgaaaatca    1200
gaagcccatg ttcgagctgg ctgaaggcgc tacgttgaag aatgtgaacc tgggtgagaa    1260
cgaggtcgat ggcatccacg tgaaagccaa aaacgctcag gaagtcacca ttgacaacgt    1320
gcatgcccag aacgtcggtg aagacctgat tacggtcaaa ggcgagggag gcgcagcggt    1380
cactaatctg aacatcaaga acagcagtgc caaaggtgca gacgacaagg ttgtccagct    1440
caacgccaac actcacttga aaatcgacaa cttcaaggcc gacgatttcg gcacgatggt    1500
tcgcaccaac ggtggcaagc agtttgatga catgagcatc gagctgaacg gcatcgaagc    1560
taaccacggc aagttcgccc tggtgaaaag cgacagtgac gatctgaagc tggcaacggg    1620
caacatcgcc atgaccgacg tcaaacacgc ctacgataaa acccaggcat cgacccaaca    1680
caccgagctt tgaatccaga caagtagctt gaaaaaaggg ggtggactc                1729
```

<210> SEQ ID NO 11
<211> LENGTH: 344
<212> TYPE: PRT
<213> ORGANISM: Pseudomonas solanacearum

<400> SEQUENCE: 11

```
Met Ser Val Gly Asn Ile Gln Ser Pro Ser Asn Leu Pro Gly Leu Gln
1               5                   10                  15

Asn Leu Asn Leu Asn Thr Asn Thr Asn Ser Gln Gln Ser Gly Gln Ser
            20                  25                  30

Val Gln Asp Leu Ile Lys Gln Val Glu Lys Asp Ile Leu Asn Ile Ile
        35                  40                  45

Ala Ala Leu Val Gln Lys Ala Ala Gln Ser Ala Gly Gly As

```
Ala Gln Gly Gly Ser Lys Gly Ala Gly Asn Ala Ser Pro Ala Ser Gly
        275                 280                 285

Ala Asn Pro Gly Ala Asn Gln Pro Gly Ser Ala Asp Asp Gln Ser Ser
        290                 295                 300

Gly Gln Asn Asn Leu Gln Ser Gln Ile Met Asp Val Val Lys Glu Val
305                 310                 315                 320

Val Gln Ile Leu Gln Gln Met Leu Ala Ala Gln Asn Gly Gly Ser Gln
        325                 330                 335

Gln Ser Thr Ser Thr Gln Pro Met
        340

<210> SEQ ID NO 12
<211> LENGTH: 1035
<212> TYPE: DNA
<213> ORGANISM: Pseudomonas solanacearum

<400> SEQUENCE: 12
atgtcagtcg aaacatcca gagcccgtcg aacctcccgg gtctgcagaa cctgaacctc      60
aacaccaaca ccaacagcca gcaatcgggc cagtccgtgc aagacctgat caagcaggtc     120
gagaaggaca tcctcaacat catcgcagcc ctcgtgcaga aggccgcaca gtcggcgggc     180
ggcaacaccg gtaacaccgg caacgcgccg gcgaaggacg gcaatgccaa cgcgggcgcc     240
aacgacccga gcaagaacga cccgagcaag agccaggctc gcagtcggc caacaagacc     300 ggcaacgtcg acgacgccaa caaccaggat ccgatgcaag cgctgatgca gctgctggaa     360
gacctggtga gctgctgaa gcggcccctg cacatgcagc agcccggcgg caatgacaag     420
ggcaacggcg tgggcggtgc caacggcgcc aagggtgccg gcggccaggg cggcctggcc     480
gaagcgctgc aggagatcga gcagatcctc gcccagctcg gcggcggcgg tgctggcgcc     540
ggcggcgcgg gtggcggtgt cggcggtgct ggtggcgcgg atggcggctc cggtgcgggt     600
ggcgcaggcg gtgcgaacgg cgccgacggc ggcaatggcg tgaacggcaa ccaggcgaac     660
ggcccgcaga acgcaggcga tgtcaacggt gccaacggcg cggatgacgg cagcgaagac     720
cagggcggcc tcaccggcgt gctgcaaaag ctgatgaaga tcctgaacgc gctggtgcag     780
atgatgcagc aaggcggcct cggcggcggc aaccaggcgc agggcggctc gaagggtgcc     840
ggcaacgcct cgccggcttc cggcgcgaac ccgggcgcga accagcccgg ttcggcggat     900
gatcaatcgt ccggccagaa caatctgcaa tcccagatca tggatgtggt gaaggaggtc     960
gtccagatcc tgcagcagat gctggcggcg cagaacggcg gcagccagca gtccacctcg    1020
acgcagccga tgtaa                                                     1035

<210> SEQ ID NO 13
<211> LENGTH: 114
<212> TYPE: PRT
<213> ORGANISM: Xanthomonas campestris

<400> SEQUENCE: 13

Met Asp Ser Ile Gly Asn Asn Phe Ser Asn Ile Gly Asn Leu Gln Thr
1               5                   10                  15

Met Gly Ile Gly Pro G

-continued

```
65                  70                  75                  80

Thr Gln Met Leu Met Gln Ile Val Met Gln Leu Met Gln Asn Gln Gly
                85                  90                  95

Gly Ala Gly Met Gly Gly Gly Gly Ser Val Asn Ser Ser Leu Gly Gly
            100                 105                 110

Asn Ala

<210> SEQ ID NO 14
<211> LENGTH: 342
<212> TYPE: DNA
<213> ORGANISM: Xanthomonas campestris
<400> SEQUENCE: 14
atggactcta tcggaaacaa cttttcgaat atcggcaacc tgcagacgat gggcatcggg      60
cctcagcaac acgaggactc cagccagcag tcgccttcgg ctggctccga gcagcagctg     120
gatcagttgc tcgccatgtt catcatgatg atgctgcaac agagccaggg cagcgatgca     180
aatcaggagt gtggcaacga acaaccgcag aacggtcaac aggaaggcct gagtccgttg     240
acgcagatgc tgatgcagat cgtgatgcag ctgatgcaga accagggcgg cgccggcatg     300
ggcggtggcg gttcggtcaa cagcagcctg ggcggcaacg cc                        342
```